United States Patent
Trajkovski et al.

(10) Patent No.: US 11,541,083 B2
(45) Date of Patent: Jan. 3, 2023

(54) METHODS AND PROBIOTIC COMPOSITIONS FOR THE TREATMENT OF BONE DISORDERS

(71) Applicant: Research Development Foundation, Carson City, NV (US)

(72) Inventors: Mirko Trajkovski, Geneva (CH); Claire Chevalier, Geneva (CH)

(73) Assignee: Research Development Foundation, Carson City, NV (US)

( * ) Notice: Subject to any disclaimer, the term of this patent is extended or adjusted under 35 U.S.C. 154(b) by 68 days.

(21) Appl. No.: 16/585,726

(22) Filed: Sep. 27, 2019

(65) Prior Publication Data

US 2020/0101121 A1 Apr. 2, 2020

Related U.S. Application Data

(60) Provisional application No. 62/737,661, filed on Sep. 27, 2018.

(51) Int. Cl.
| | | |
|---|---|---|
| *A61P 19/10* | (2006.01) | |
| *A61K 35/741* | (2015.01) | |
| *A61K 35/747* | (2015.01) | |
| *A61K 47/69* | (2017.01) | |
| *A61K 47/36* | (2006.01) | |

(52) U.S. Cl.
CPC .......... *A61K 35/747* (2013.01); *A61K 47/36* (2013.01); *A61K 47/6903* (2017.08); *A61P 19/10* (2018.01)

(58) Field of Classification Search
CPC ...... A61P 19/10; A61K 35/741; A61K 35/745
See application file for complete search history.

(56) References Cited

U.S. PATENT DOCUMENTS

| 8,501,169 | B2 * | 8/2013 | Sanz Herranz | A23L 33/135 |
|---|---|---|---|---|
| | | | | 424/93.4 |
| 2003/0125649 | A1 | 7/2003 | McIntosh et al. | |
| 2016/0040215 | A1 | 2/2016 | Henn et al. | |
| 2016/0106574 | A1 | 4/2016 | Stewart | |
| 2016/0331792 | A1 | 11/2016 | Dominguez-Bello | |
| 2017/0354695 | A1 | 12/2017 | Grant et al. | |

FOREIGN PATENT DOCUMENTS

| DE | 10 2010 056 029 | 6/2012 | |
|---|---|---|---|
| WO | WO 1998/031310 | 7/1998 | |
| WO | WO-2016203220 A1 * | 12/2016 | ............. A61K 35/74 |
| WO | WO 2018/094190 | 5/2018 | |
| WO | WO 2019/051380 | 3/2019 | |

OTHER PUBLICATIONS

Osteoporosis. What is osteoporosis and what causes it? National Osteoporosis Foundation. 2016;1-3.*

Ji et al. Primary osteoporosis in postmenopausal women. Chronic Diseases and Translational medicine. 2015;9-13.*

Alhilli and Wright, "The Effects of Changes in the Environmental Temperature on the Growth of Tail Bones in the Mouse," *British Journal of Experimental Pathology*, 64(1): p. 34-42, 1983.

Britton et al., "Probiotic L. Reuteri Treatment Prevents Bone Loss in a Menopausal Ovariectomized Mouse Model," *Journal of Cellular Physiology*, 2014. 229(11): p. 1822-1830, 2014.

Calinescu et al., "Carboxymethyl high amylose starch (CM-HAS) as excipient for *Escherichia coli* oral formulations," *Eur J Pharm Biopharm.*, 60(1):53-60, 2005.

Caporaso et al., "Global patterns of 16S rRNA diversity at a depth of millions of sequences per sample," *Proceedings of the National Academy of Sciences of the United States of America*, 108: p. 4516-4522, 2011.

Caporaso et al., "Ultra-high-throughput microbial community analysis on the Illumina HiSeq and MiSeq platforms," *Isme Journal*, 6(8): p. 1621-1624, 2012.

Chelakkot et al., "Akkermansia muciniphila-derived extracellular vesicles influence gut permeability through the regulation of tight junctions," *Experimental & Molecular Medicine* vol. 50, p. e450, 2018.

Chevalier et al., "Gut Microbiota Orchestrates Energy Homeostasis during Cold," *Cold. Cell*, 163(6): p. 1360-74, 2015.

Choi et al., "Gut microbe-derived extracellular vesicles induce insulin resistance, thereby impairing glucose metabolism in skeletal muscle," *Sci Rep*, 5: 15878, 2015.

Dar et al., "*Lactobacillus acidophilus* inhibits bone loss and increases bone heterogeneity in osteoporotic mice via modulating Treg-Th17 cell balance," *Bone Rep*, 8: p. 46-56, 2018.

de Bakker et al., "Effects of reproduction on sexual dimorphisms in rat bone mechanics," *J Biomech*, Aug. 22;77:40-47, 2018.

Derrien et al., "*Akkermansia muciniphila* gen. nov., sp. nov., a human intestinal mucin-degrading bacterium," *Int J Syst Evol Microbiol*, 54: 1469-1476, 2004.

Devlin et al., "Caloric restriction leads to high marrow adiposity and low bone mass in growing mice," *Journal of Bone and Mineral Research*, 2010. 25(9): p. 2078-2088, 2010.

Ellis and Kuehn, "Virulence and immunomodulatory roles of bacterial outer membrane vesicles," *Microbiol Mol Biol Rev.*, 74: 81-94, 2010.

Fabbiano et al., "Caloric Restriction Leads to Browning of White Adipose Tissue through Type 2 Immune Signaling," *Cell Metab*, 24(3): p. 434-46, 2016.

Fabbiano et al., "Functional Gut Microbiota Remodeling Contributes to the Caloric Restriction-Induced Metabolic Improvements," *Cell metabolism*, In press, 28(6):907-921.e7., 2018.

Govender et al., "A review of the advancements in probiotic delivery: Conventional vs. non-conventional formulations for intestinal flora supplementation," *AAPS PharmSciTech*, 15(1):29-43, 2014.

(Continued)

*Primary Examiner* — Lynn Y Fan

(74) *Attorney, Agent, or Firm* — Parker Highlander PLLC

(57) ABSTRACT

In some aspects, methods and probiotic compositions are provided for the treatment of bone diseases such as, e.g., ostetoporosis. In some embodiments, one or more bacteria from the warm microbiota such as, e.g., *Clostridialeace-assimilate*, *Lactobacillus*, *Bifidobacteriaceae*, *Akkermansia*, and/or *Parabacteroides* may be administered to a subject, such as a human subject, to treat the bone disease. In some embodiments, heat may be applied to the subject to promote the development of warm microbiota to treat the bone disease.

30 Claims, 7 Drawing Sheets

Specification includes a Sequence Listing.

(56) References Cited

OTHER PUBLICATIONS

Hong et al., "Extracellular vesicles derived from *Staphylococcus aureus* induce atopic dermatitis-like skin inflammation," *Allergy*, 66: 351-359, 2011.
Horstman and Kuehn, "Bacterial surface association of heat-labile enterotoxin through lipopolysaccharide after secretion via the general secretory pathway," *J Biol Chem.*,277: 32538-32545, 2002.
Hussan et al., *Journal of Pharmacy* 2(6):5-11, 2012.
International Search Report for PCT/US2019/053402, dated Dec. 13, 2019.
Iwaniec and Turner, "Influence of body weight on bone mass, architecture and turnover," *J Endocrinol*, 2016. 230(3): p. R115-30.
Iwasa et al., "The effects of ovariectomy and lifelong high-fat diet consumption on body weight, appetite, and lifespan in female rats," *Horm Behav*, 97: p. 25-30, 2018.
Jansman et al., "Effects of a Simple or a Complex Starter Microbiota on Intestinal Microbiota Composition in Caesarean Derived Piglets," Journal of Animal Science, Dec. 1, 2012, vol. 90, Iss. 4, pp. 433-435.
Kaiyala et al., "Acutely decreased thermoregulatory energy expenditure or decreased activity energy expenditure both acutely reduce food intake in mice," *Plos One*, 7(8), 2012.
Kim et al., "Extracellular vesicles, especially derived from Gram-negative bacteria, in indoor dust induce neutrophilic pulmonary inflammation associated with both Th1 and Th17 cell responses," *Clin Exp Allergy*, 43: 443-454, 2013.
Kuehn and Kesty, Bacterial outer membrane vesicles and the host-pathogen interaction, *Genes Dev.*, 19: 2645-2655, 2005.
Lee et al. "Global proteomic profiling of native outer membrane vesicles derived from *Escherichia coli,*" *Proteomics*, 7: 3143-3153, 2007.
Lee et al., "Gram-positive bacteria produce membrane vesicles: proteomics-based characterization of *Staphylococcus aureus*-derived membrane vesicles," *Proteomic*, 9: 5425-5436., 2009.
Legroux-Gerot et al., "Evaluation of bone loss and its mechanisms in anorexia nervosa," *Calcified Tissue International*, 81(3): p. 174-182, 2007.
Li, et al., "Sex steroid deficiency-associated bone loss is microbiota dependent and prevented by probiotics," *Journal of Clinical Investigation*, 126(6): p. 2049-2063, 2016.
Liu et al., "Gram-Positive Bacterial Extracellular Vesicles and Their Impact on Health and Disease," Frontiers in Microbiology, Jul. 9, 2018, vol. 9, pp. 1-8.
Mcmillan et al., "Rapid changes of light microscopic indices of osteoclast-bone relationships correlated with electron microscopy," *Calcified Tissue International*, 44(6): p. 399-405, 1989.
Meyer et al., "Body Temperature Measurements for Metabolic Phenotyping in Mice," *Frontiers in Physiology*, 8:520, 2017.
Nilsson et al., "Lactobacillus reuteri reduces bone loss in older women with low bone mineral density: a randomized, placebo-controlled, double-blind, clinical trial," *J Intern Med*, 2018, 284(3):307-317.
Ohlsson and Sjogren, "Effects of the gut microbiota on bone mass," *Trends Endocrinol Metab*, 2015, 26(2): p. 69-74.
Reginster and Burlet, "Osteoporosis: a still increasing prevalence," *Bone*, 38(2): p. 4-9, 2006.
Romsos, et al., "Effects of a warm environment on energy balance in obese (ob/ob) mice," *Metabolism—Clinical and Experimental*, 34(10): p. 931-937, 1985.
Sanderson et al., "Influence of fat intake and caloric restriction on bone in aging male rats," *Journals of Gerontology Series a—Biological Sciences and Medical Sciences*, 52(1): p. B20-B25, 1997.
Serrat, et al., "Temperature regulates limb length in homeotherms by directly modulating cartilage growth," *Proceedings of the National Academy of Sciences of the United States of America*, 105(49): p. 19348-19353, 2008.
Serrat, et al., "Unilateral heat accelerates bone elongation and lengthens extremities of growing mice," *Journal of Orthopaedic Research*, 33(5): p. 692-698, 2015.
Sjogren et al., "The gut microbiota regulates bone mass in mice," *J Bone Miner Res*, 27(6): p. 1357-67, 2012.
Sozen et al., "An overview and management of osteoporosis," *European Journal of Rheumatology*, 4(1): p. 46-56, 2017.
Suarez-Zamorano et al., "Microbiota depletion promotes browning of white adipose tissue and reduces obesity," Nat Med, 2015. 21(12): p. 1497-1501, 2015.
Villareal "Bone mineral density response to caloric restriction-induced weight loss or exercise-induced weight loss: a randomized controlled trial," *Arch Intern Med*, 166(22): p. 2502-10, 2006.
Wilson et al. "The Super-Donor Phenomenon in Fecal Microbiota Transplantation," *Front Cell Infect Microbiol.* 9: 2, 2019.
Worthmann "Cold-induced conversion of cholesterol to bile acids in mice shapes the gut microbiome and promotes adaptive thermogenesis," *Nat Med*, 23(7): p. 839-849, 2017.
Yang et al., "Colon-specific drug delivery: new approaches and in vitro/in vivo evaluation," 235(1-2):1-15, 2002.
Zietak "Altered Microbiota Contributes to Reduced Diet-Induced Obesity upon Cold Exposure," *Cell Metabolism*, 23(6): p. 1216-1223, 2016.
Aguilar-Toalá et al., "Postbiotics: An evolving term within the functional foods field," *Trends in Food Science & Technology*, 75:105-114, 2018.
Food and Agriculture Organisation of the United Nations and World Health Organisation, "Health and nutritional properties of probiotics in food including powder milk with live active lactic acid bacteria. Report of joint FAO/WHO Expert Consultation on evaluation and health and nutritional properties of probiotics in food including powder milk with live lactic acid bacteria," FAO Food and Nutrition Paper 85, FAO/WHO, 2001.
Terpou et al., "Probiotics in food systems: significance and emerging strategies towards improved viability and delivery of enhanced beneficial value," *Nutrients*, 11(1591):1-32, 2019.
"A bacteria likely to reduce the cardiovascular risks of 1 in 2 people," UCLouvain Press Release, Jul. 1, 2019.
"Evaluation of the Effects Associated With the Administration of Akkermansia Muciniphila on Parameters of Metabolic Syndrome (Microbes4U)," ClinicalTrials.gov, Sponsor: Patrice Cani, first posted Dec. 22, 2015, last updated May 17, 2019.
"First clinical trial finds probiotic treatment with dead bacteria is better than placebo at alleviating symptoms of IBS," located at https://medicalxpress.com/news/2020-04-clinical-trial-probiotic-treatment-dead.html, Apr. 9, 2020.
Andresen et al., "Heat-inactivated Bifidobacterium bifidum MIMBb75 (SYN-HI-001) in the treatment of irritable bowel syndrome: a multicentre, randomised, double-blind, placebo-controlled clinical trial," *The Lancet*, 5(7):658-666, 2020.
Aponte et al., "Therapeutic, prophylactic, and functional use of probiotics: a current perspective," *Front. Microbiol.*, 11:562048, 2020.
Baltic, "Inactivated probiotic effective against irritable bowel syndrome," *Reuters Health*, 2020.
Cani, "Akkermansia muciniphila helps improve features of metabolic syndrome in overweight and obese subjects," *Gut Microbiota for Health*, 2019.
Cani, "Human gut microbiome: hopes, threats and promises," *Gut*, 67:1716-1725, 2018.
Cohut, "Even 'dead,' this probiotic may be effective against inflammation," *Medical News Today*, 2019.
Das, "Nonviable, Heat-inactivated Bifidobacterium bifidum MIMBb75 Improves IBS Symptoms," *Lancet Gastroenterol Hepatol.*, 2020.
Depommier et al., "Supplementation with Akkermansia muciniphila in overweight and obese human volunteers: a proof-of-concept exploratory study," *Nat Med.*, 25:1096-1103, 2019.
Lee et al., "The Effect of Lactobacillus gasseri BNR17 on Postmenopausal Symptoms in Ovariectomized Rats," *J Microbiol Biotechnol.*, 31(9):1281-1287, 2021.

(56) References Cited

OTHER PUBLICATIONS

Prados, "Current evidence-based strategies for modulating the gut microbiota: where do we stand?" *Gut Microbiota for Health*, 2020.
"Deadly Staph infections still threaten the U.S.," Centers for Disease Control and Prevention website, located at www.cdc.gov/media/releases/2019/p0305-deadly-staph-infections.html#:~:text=More%20than%20119%2C000%20people%20suffered,Control%20and%20Prevention%20(CDC), Mar. 5, 2019.
"Prevent illness from *C. perfringens*," Centers for Disease Control and Prevention website, located at www.cdc.gov/foodsafety/diseases/clostridium-perfringens.html, last reviewed May 18, 2021, accessed May 25, 2022.
Chevalier et al., "Warmth prevents bone loss through the gut microbiota," *Cell Metabolism*, 32:575-590, 2020.
Collins et al., "The potential of probiotics as a therapy for osteoporosis," *Microbiol Spectr.*, 5(4), 2017.
Gatej et al., "Probiotic *Lactobacillus rhamnosus* GG prevents alveolar bone loss in a mouse model of experimental periodontitis," *J Clin Periodontal.*, 45:204-212, 2018.
Iqbal et al., "Getting warmer: following one's gut to build bone," *Cell Metabolism*, 32:504-506, 2020.
Lambert et al., "Combined bioavailable isoflavones and probiotics improve bone status and estrogen metabolism in postmenopausal osteopenic women: a randomized controlled trial," *Am J Clin Nutr.*, 106:909-920, 2017.
Partial Supplementary European Search Report issued in European Application No. 19864106.0, dated May 20, 2022.
Robbins et al., "Low temperature decreases bone mass in mice: implications for humans," *Am J Phys Anthropol.*, 167:557-568, 2018.

\* cited by examiner

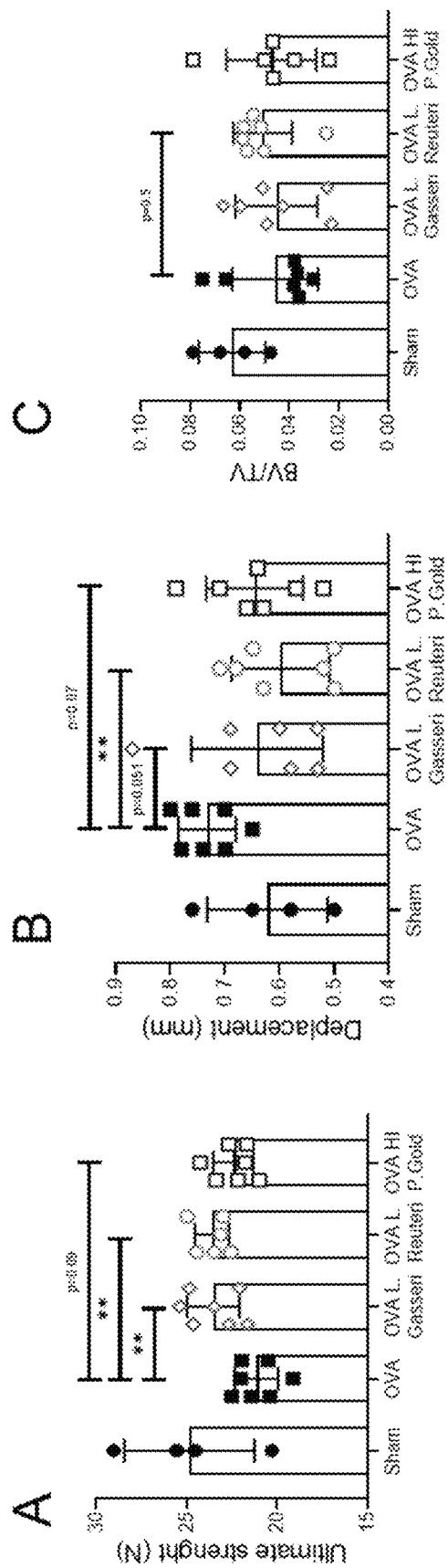
FIGS. 7A-C

US 11,541,083 B2

METHODS AND PROBIOTIC COMPOSITIONS FOR THE TREATMENT OF BONE DISORDERS

This application claims the benefit of U.S. Provisional Patent Application No. 62/737,661, filed Sep. 27, 2018, the entirety of which is incorporated herein by reference.

BACKGROUND OF THE INVENTION

1. Field of the Invention

The present invention relates generally to the fields of biology and medicine. More particularly, it concerns methods and compositions for the treatment of bone diseases.

2. Description of Related Art

Osteoporosis presents a significant clinical problem. Osteoporosis is the most prevalent metabolic bone disorders, characterized by low bone mass and microarchitectural deterioration (Sozen et al., 2017). Patients with osteoporosis have fragile bones and are vulnerable to fractures. The most common type of primary osteoporosis is due to the post-menopausal oestrogen deficiency, reflected in a higher incidence of osteoporosis in women (Reginster and Burlet, 2006). Although some therapies have been developed for the treatment of osteoporosis, some patients do not respond to these therapies and there is a need for new and improved therapies.

SUMMARY OF THE INVENTION

The present invention is based, in part, on the discovery that warm microbiota can improve bone density, strength, and other bone characteristics. In some embodiments, pharmaceutical compositions or probiotic compositions are provided that comprise one or more species of warm microbiota and may be used to treat a bone disease such as, e.g., osteoporosis.

An aspect of the present invention relates to a method for treating or preventing a bone disease or increasing bone strength in a mammalian subject, comprising administering a pharmaceutical or probiotic composition to the gastrointestinal system of the subject; wherein the composition comprises at least one warm microbiota bacteria or extracellular vesicles from at least one warm microbiota bacteria, and wherein if the warm microbiota contains *Lactobacillus reuteri, Lactobacillus acidophilus,* or *Lactobacillus rhamnosus,* then the warm microbiota contains at least one additional species of *Clostridialeace*-assimilate, *Lactobacillus, Bifidobacteriaceae,* or *Parabacteroides* genera. In some embodiments, the composition comprises *Lactobacillus gasseri, Lactobacillus reuteri,* and/or *Parabacteroides goldsteinii* (e.g., heat-inactivated *Parabacteroides goldsteinii*). In some embodiments, the composition comprises extracellular vesicles from *Lactobacillus gasseri, Lactobacillus reuteri,* and/or *Parabacteroides goldsteinii* (e.g., heat-inactivated *Parabacteroides goldsteinii,* or living *Parabacteroides goldsteinii*). Preferably, a therapeutically effective amount of the warm microbiota or the extracellular vesicles is administered to the subject. In some embodiments, the composition comprises from about $1\times10^8$ to about $1\times10^{13}$ cfu of the warm microbiota bacteria. In some embodiments, the warm microbiota comprises *Clostridialeace*-assimilate spp., *Lactobacillus* spp., *Bifidobacteriaceae* spp., and/or *Parabacteroides* spp. In some embodiments, the warm microbiota comprises (*Lactobacillus* spp. and *Parabacteroides* spp.) or (*Lactobacillus* spp. and *Bifidobacteriaceae* spp.). In some embodiments, the warm microbiota comprises *Clostridialeace*-assimilate spp., *Lactobacillus* spp., and *Parabacteroides* spp. The ratios of bacteria in the warm microbiota may be about 10-40% (e.g., 10, 15, 20, 25, 30, 35, 40%, or any range derivable therein) *Clostridialeace*-assimilate spp., about 40-60% (e.g., 40, 45, 50, 55, 60%, or any range derivable therein) *Lactobacillus* spp., and about 10-40% (e.g., 10, 15, 20, 25, 30, 35, 40%, or any range derivable therein) *Parabacteroides* spp. In some embodiments, the ratios of bacteria in the warm microbiota are about 10-35% *Clostridialeace*-assimilate spp., about 40-60% *Lactobacillus* spp., and about 20-30% *Parabacteroides* spp. The warm microbiota may comprise *Bifidobacteriaceae* such as (e.g., *Bifidobacterium longum*) or *Akkermansia muciniphila*. The warm microbiota may comprise or consist essentially of live bacteria. The warm microbiota may comprise or consist essentially of heat-inactivated bacteria. The warm microbiota may comprise or consist of frozen or dried bacteria. In some embodiments, the composition comprises extracellular vesicles from warm microbiota.

In some embodiments, the pharmaceutical or probiotic composition is administered orally, colonically, via enema, via an orogastric tube, or via a nasogastric tube. In some embodiments, the warm microbiota is comprised in a pharmaceutical or probiotic composition that is resistant to degradation in the stomach but releases bacteria in the small intestine and/or large intestine of the subject. The pharmaceutical or probiotic composition may comprise an enteric coating, chitosan-alginate beads, or a hydrogel. The enteric coating may be a fatty acid, a wax, a shellac, a plastic such as a phthalate, CAP, CAT, PVAP, HPMCP, or a plant fiber. In some embodiments, the pharmaceutical or probiotic composition does not comprise an enteric coating. In some embodiments, the pharmaceutical or probiotic composition is a tablet or capsule. The subject may be a human. In some embodiments, the method comprises obtaining the warm microbiota from a super donor or a separate healthy subject (e.g., a separate healthy subject who does not have a bone disease). Super-donors are individuals who have been identified as having particularly beneficial microbiota diversity and composition (e.g., Wilson et al., 2019). The method may comprise obtaining the warm microbiota from the subject during the spring or summer and administering the warm microbiota to the subject during the winter. The warm microbiota may be frozen after the obtaining and prior to administering to the subject. In some embodiments, the subject has a bone disease, e.g., osteoporosis, osteomalacia, osteolysis, osteochondrodysplasias, periodontitis, rheumatoid arthritis, metabolic bone disease, a parathyroid disorder, steroid-induced osteoporosis, chemotherapy-induced bone loss, pre-menopausal bone loss, fragility and recurrent fractures, renal osteodystrophy, or Paget's disease. In some embodiments, the bone disease is osteoporosis.

Another aspect of the present invention relates to a pharmaceutical or probiotic composition for delivery to the gastrointestinal system comprising *Clostridialeace*-assimilate spp., *Lactobacillus* spp., *Bifidobacteriaceae* spp., and/or *Parabacteroides* spp., or combinations thereof; wherein if the warm microbiota contains *Lactobacillus reuteri, Lactobacillus acidophilus,* or *Lactobacillus rhamnosus,* then the warm microbiota contains at least one additional species of *Clostridialeace*-assimilate, *Lactobacillus, Bifidobacteriaceae,* or *Parabacteroides*. The warm microbiota may comprise *Clostridialeace*-assimilate spp., *Lactobacillus* spp.,

*Parabacteroides* spp., and/or *Akkermansia muciniphila*. The warm microbiota may comprise *Lactobacillus* spp. and *Parabacteroides* spp. In some embodiments, the warm microbiota comprises *Clostridialeace*-assimilate spp., *Lactobacillus* spp., and *Parabacteroides* spp, optionally further comprising *Akkermansia muciniphila*. The ratios of bacteria in the warm microbiota may be about 10-40% (e.g., 10, 15, 20, 25, 30, 35, 40%, or any range derivable therein) *Clostridialeace*-assimilate spp., about 40-60% (e.g., 40, 45, 50, 55, 60%, or any range derivable therein) *Lactobacillus* spp., and about 10-40% (e.g., 10, 15, 20, 25, 30, 35, 40%, or any range derivable therein) *Parabacteroides* spp. The ratios of bacteria in the warm microbiota may be about 10-35% *Clostridialeace*-assimilate spp., about 40-60% *Lactobacillus* spp., and about 20-30% *Parabacteroides* spp. The warm microbiota may comprise *Bifidobacteriaceae*, e.g., *Bifidobacterium longum*. The warm microbiota may comprise or consist essentially of live bacteria, heat-inactivated bacteria, and/or frozen or dried bacteria. In some embodiments, the composition comprises extracellular vesicles from the warm microbiota. The pharmaceutical or probiotic composition may be formulated for oral, colonic, enema, orogastric, or nasogastric administration. The pharmaceutical or probiotic composition may be resistant to degradation in the stomach but releases bacteria in the small intestine and/or large intestine of the subject. The pharmaceutical or probiotic composition may comprise an enteric coating, chitosan-alginate beads, or a hydrogel. The enteric coating may be a fatty acid, a wax, a shellac, a plastic such as a phthalate, CAP, CAT, PVAP, HPMCP, or a plant fiber. In some embodiments, the pharmaceutical or probiotic composition does not comprise an enteric coating. In some embodiments, the pharmaceutical or probiotic composition is a tablet or capsule.

The composition may be used in treating a bone disorder in a mammalian subject, e.g., osteoporosis, osteomalacia, osteolysis, osteochondrodysplasias, periodontitis, rheumatoid arthritis, metabolic bone disease, a parathyroid disorder, steroid-induced osteoporosis, chemotherapy-induced bone loss, pre-menopausal bone loss, fragility and recurrent fractures, renal osteodystrophy, or Paget's disease. The subject may be a human.

Yet another aspect of the present invention relates to a method of treating or preventing a bone disorder in a mammalian subject comprising administering heat to the torso, whole body, and/or extremities of the subject. The method may comprise having the subject remain in a climate chamber with an ambient temperature of from about 65° C. to about 95° C. for about 3-20 minutes, about 3-15 minutes, about 3-10 minutes, or about 3-5 minutes. In some embodiments, the subject is repeatedly exposed to the climate chamber, with periods of time between each exposure (e.g., a period of about 10 minutes to 1, 2, 3, 4, 5 hours or about 1, 2, 3, 4, 5, 6 days or 1 about week between exposures). For example, the subject may be repeatedly exposed to ambient conditions of about 65-95° C. or 70-95° C. for about 3-15 minutes (e.g., about 5 minutes) during each exposure. The climate chamber may have an ambient temperature of from about 65° C. to about 95° C., and subject may remain in the climate chamber for about 3-30 minutes, about 3-15 minutes, about 3-10 minutes, or about 3-5 minutes. The method may comprise applying a heating pad or heating lamp (e.g., an infrared lamp) to the torso, stomach, and/or abdomen (or any targeted zone for treatment) of the subject, wherein the heating pad is from about 27° C. to about 36° C. (e.g., from about 27-50, 27-95, 65-95, or 35-50° C.) or wherein the heating lamp is from about 60° C. to about 95° C. In some embodiments, a heating pad of about 27-36° C. is applied to the body region for a duration of at least 10 minutes to several hours (e.g., about 1, 2, 3, 4, or 5 hours). In some embodiments, a warmer heating pad of about 36-95 or 35-50° C. is applied to the body region for a shorter period of time such as, e.g., about 3-15 minutes. In some embodiments, the heating pad is used to raise the surface temperature of the particular body region to about 27-36 or 27-39° C. The method may comprise placing the subject in a warm climatized environment, wherein the temperature is from about 30-85° C., more preferably about 32-80° C. The heat may be applied for a period of from about 3 minutes to about 9 hours, or 30 minutes to about 9 hours, or from 1-12 hours, or any range derivable therein (e.g., 3-10 minutes, 10-30 minutes, 10 minutes-3 hours, etc.). The heat may be applied at least 1, 2, 3, 4, 5, 6, or 7 days a week for 1, 2, 3, 4, 5, 6, 7, 8, 9, or more weeks. The bone disorder may be osteoporosis, osteomalacia, osteolysis, or osteochondrodysplasias. In some embodiments, the bone disorder is osteoporosis.

*Lactobacillus gasseri* is a species of bacteria that has been identified as part of the vaginal flora and has been found in the lower digestive systems of women. Particular strains of *Lactobacillus gasseri* that may be used to treat a bone disease or increase bone strength in a mammalian subject can include DSM 20077, DSM 107525, DSM 20243, DSM 20604, ATCC® 3332, ATCC® 2960, ATCC® BAA-2841, ATCC® PTA4483, ATCC® PTA4481, ATCC® PTA4484, ATCC® PTA4480, and/or ATCC® PTA4479. A variety of amounts of *Lactobacillus gasseri* may be administered to a mammalian subject (e.g., a human) to treat a bone disorder as described herein (e.g., osteoporosis, etc.). For example, in some embodiments from about $1 \times 10^8$ to about $1 \times 10^{13}$ cfu of *Lactobacillus gasseri* can be administered to a mammalian subject, such as a human, to treat the bone disorder or promote bone strengthening.

*Lactobacillus reuteri* is a species of bacteria that has been found in the intestinal tract of healthy mammals. Particular strains of *Lactobacillus reuteri* that may be used to treat a bone disease or increase bone strength in a mammalian subject include DSM 100191, DSM 100192, DSM 17509, DSM 20015, DSM 20016, DSM 20053, DSM 20056, DSM 28673, DSM 32035, ATCC® BAA-2837™, ATCC® 55148, ATCC® 53608, ATCC® 23272, ATCC® 23272D5, and/or ATCC® PTA6475. A variety of amounts of *Lactobacillus reuteri* may be administered to a mammalian subject (e.g., a human) to treat a bone disorder as described herein (e.g., osteoporosis, etc.). For example, in some embodiments from about $1 \times 10^8$ to about $1 \times 10^{13}$ cfu of *Lactobacillus reuteri* can be administered to a mammalian subject, such as a human, to treat the bone disorder or promote bone strengthening.

*Parabacteroides goldsteinii* is a gram-negative, obligately anaerobic non-spore-forming and non-motile bacterium that has been isolated from human blood. Particular strains of *Parabacteroides goldsteinii* that may be used to treat a bone disease or increase bone strength in a mammalian subject include DSM 19448 and/or DSM 29187. A variety of amounts of *Parabacteroides goldsteinii* may be administered to a mammalian subject (e.g., a human) to treat a bone disorder as described herein (e.g., osteoporosis, etc.). For example, in some embodiments from about $1 \times 10^8$ to about $1 \times 10^{13}$ cfu of *Parabacteroides goldsteinii* can be administered to a mammalian subject, such as a human, to treat the bone disorder. As shown in the below examples, heat-inactivated *Parabacteroides goldsteinii* can be administered to treat a bone disorder or promote bone strengthening. Methods of heat inactivation that may be used to prepare heat-inactivated *Parabacteroides goldsteinii* are well known and include heating up the bacteria to 100° C. for 15 min (Wu et al., 2019).

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. A petition for color drawings is provided herewith. The color in the drawings is important, e.g., for observation of the different groups of bacteria in FIGS. 1D-E.

(FIG. 1A) Body weight gain of mice exposed to 34° C. for 1 month, and control mice kept at room temperature (RT). (n=8 males per groups). (FIG. 1B) Food intake of the mice as in A. (FIG. 1C) Principal coordinates analysis (PcoA) of 16SrDNA sequencing of fecal samples of mice exposed for 1 month to 34° C. and their RT controls as in FIG. 1A. Each symbol represents a mouse's fecal microbiota. The analysis is based on Weighted UNIFRAC distance calculation. (FIG. 1D) Barchart representing the family proportional abundance of the samples as in FIG. 1C. (FIG. 1E) Heatmap showing OTUs associated with a p-value <0.05 after Kruskal-Walis test between 34° C. exposed mice's and RT controls' fecal microbiota. Plotted is a z-score computed on the relative abundances of the selected OTUs. An idealized tree represents their taxonomic hierarchy. Final leaves are labelled with the corresponding family name. Each column represents one mouse's fecal microbiota. (FIG. 1F) Shannon diversity and estimated richness (observed OTUs) in the samples as in FIG. 1C. Data are displayed as mean±SD. (FIG. 1G) Principal coordinate analysis of the fecal samples of the donor mice as in FIG. 1C. (1 month exposed at 34° C. and their RT controls) and of the microbiota of corresponding recipient mice, kept at RT for 20 days. (n=10/group for the transplanted, n=8/group for the donors).

(FIG. 2A) Eye temperature of mice 26 days after being exposed to 34° C. and their RT controls (n=8 males per groups). (FIG. 2B) Tail temperature measurements of mice as in FIG. 2A. (FIG. 2C) Eye temperature of mice transplanted with the gut microbiota of mice as in FIG. 2A. and kept at RT (day 16 post-transplantation). (FIG. 2D) Tail temperature of mice as in FIG. 2C. (FIGS. 2E & 2F) mRNA relative expression of brown adipose tissue markers in BAT (FIG. 2E) and beige adipose tissue markers and SAT (FIG. 2F) of mice as in FIG. 2A normalized to RT controls. (FIG. 2G) H&E staining of brown adipose tissue and subcutaneous adipose tissue of mice as in FIG. 2A. (scale: 100 µm). (FIG. 2H) Fat and lean mass percentage of total body weight, measured by EcoMRI of mice as in FIG. 2A. (FIGS. 2I & 2J) mRNA relative expression of brown adipose tissue markers in BAT (FIG. 2I) and beige adipose tissue markers and SAT (FIG. 2J) of mice as in FIG. 2A normalized to RT controls. (FIG. 2K) H&E staining of brown adipose tissue and subcutaneous adipose tissue of mice as in FIG. 2C (scale: 100 µm). (FIG. 2L) Fat and lean mass percentage of total body weight, measured by EcoMRI of mice as in FIG. 2C. (FIGS. 2M-2S) Glucose uptake in fat tissue (FIG. 2M) BAT, (FIG. 2N) SAT and (FIG. 2O) VAT, and in muscles (FIG. 2P) Soleus, (FIG. 2Q) EDL, (FIG. 2R) Gastrocnemius, and (FIG. 2S) Quadriceps after an ipGTT spiked with radiolabeled glucose of mice as in FIG. 2A and FIG. 2C. Data are displayed as mean±SD for all panels except for the qPCR data displayed as mean±SEM; n=10/group for the transplanted, n=8/group for the donors. Statistic are calculated based on Mann-Whitney t-test *>0.05, >0.01, *>0.001.

(FIGS. 3A & 3B) Tail (FIG. 3A) and femur (FIG. 3B) length of mice after 1 month at 34° C. compared to their RT-kept controls (n=8 males per group). (FIG. 3C) Bone volume density (BV/TV), measured proximally in the trabecular bone of the femur (normalized to the body weight), and associated representative pictures (scale: 200 µm), of mice as in A. (FIG. 3D) Cortical bone volume and width, measured in the midshaft of the femur (normalized to the body weight), and associated representative pictures (scale: 1 mm), of the mice as in FIG. 3A. (FIG. 3E) Biomechanical analysis of the femur using a 3-point bending test after 1 month of warm exposure, in male mice as in FIG. 3A. The parameters measured include the yield point, the ultimate stress, the elastic energy, the energy to fracture and the Young's modulus. (FIG. 3F) Same measures as in FIG. 3E on tibias of female mice (22 weeks old) exposed for 2 months at 34° C. and their RT controls (n=8 male per groups). (FIG. 3G) Tail and femur length of mice transplanted with microbiota of mice as in FIG. 3A, 20 days after the transplantation (n=10 male per groups). (FIG. 3H) Bone volume density (BV/TV), measured proximally in trabecular bone of the femur, and associated representative pictures (scale: 200 µm), of mice as in FIG. 3G. (FIG. 3I) Cortical bone volume and width, measured in the midshaft of the femur, and associated representative pictures (scale: 1 mm) of mice as in FIG. 3G. (FIG. 3J) Biomechanical analysis of the femur using a 3-point bending test after 1 month of warm exposure in male mice as in G. The parameters measured the yield point, the ultimate stress, the elastic energy, the energy to fracture and the Young's modulus. (FIG. 3K) Glucose uptake in the femur after an ipGTT spiked with radiolabeled glucose of mice as in FIG. 3A and FIG. 3G. Data are displayed as mean±SD; n=10/group for the transplanted, n=8/group for the donors. Statistic are calculated based on Mann-Whitney t-test *>0.05, >0.01, *>0.001.

(FIG. 4B) Cortical bone volume and width microarchitecture, measured in the midshaft of the tibias of mice as in FIG. 3C. (FIG. 4C) femur length of mice as in FIG. 3C associated with an extra control group of mice pair-fed like the 34° C. exposed mice but maintained at RT. (FIG. 4D) Bone volume density (BV/TV), measured proximally in the trabecular bone of the femur, in mice as in FIG. 4C. (FIG. 4E) Cortical bone volume and width microarchitecture, measured in the midshaft of the of mice as in FIG. 4C. (FIG. 4F) Biomechanical analysis of the femur using a 3-point bending test after 1 month of warm exposure in male mice as in FIG. 4A. The parameters measured include the yield point, the ultimate stress, the elastic energy, the energy to fracture and the Young's modulus. (FIG. 4G) Bone volume density (BV/TV), measured proximally in the trabecular bone of the tibias, in transplanted mice as in FIG. 3G. (FIG. 4H) Cortical bone volume and width, measured in the midshaft of the tibias in transplanted mice as in FIG. 3G. (FIG. 4I) Glucose uptake in the femur and (FIG. 4J) in the caudal vertebra measured by micro-PET-CT with [18F] fluorodeoxyglucose after overnight fasting of mice as in the FIG. 3A. (FIG. 4K) Glucose uptake as in FIG. 4I and FIG. 4J, in mice transplanted as in FIG. 3G. Data are displayed as mean±SD; n=8/group for all panels except for the transplanted n=10/group. Statistic are calculated based on Mann-Whitney t-test *>0.05, >0.01, *>0.001.

(FIG. 5A) Body weight gain of mice exposed to 34° C. for 2 months either ovariectomized or sham-operated, and their RT controls (n=8 females per groups). (FIG. 5B) food intake of mice as in FIG. 5A. (FIG. 5C) Bone volume density (BV/TV), measured proximally in the trabecular bone of the tibias (normalized to the body weight) of mice as in FIG. 5A. (FIG. 5D) Cortical bone volume and width, measured in the midshaft of the tibias (normalized to the body weight), of mice as in FIG. 5A. (FIG. 5E) Biomechanical analysis of the tibia using a 3-point bending in mice as in FIG. 5A. The parameters measured include the yield point, the ultimate stress, the elastic energy, the energy to fracture and the Young's modulus. (FIG. 5F) Tail length of mice as in FIG. 5A. (FIG. 5G) Bone volume density (BV/TV), measured in the caudal vertebra (CA2) (normalized to the body weight) of mice as in FIG. 5A. (FIG. 5H) Glucose uptake in the caudal vertebra and (FIG. 5I) in the femur measured by micro-PET-CT with [18F]fluorodeoxyglucose injection after overnight fasting of mice as in FIG. 5A. Data are displayed as mean±SD; n=8/group. Statistic are calculated based on Mann-Whitney t-test *>0.05, >0.01, *>0.001.

(FIG. 6A) Schematic representation of the experimental plan. Mice previously exposed to 34° C. for 1 month and their RT controls were used as donors of microbiota, transplanted every second day into ovariectomized recipient mice. (FIGS. 6B & 6C) Tibias of the mice were measured with a micro-CT just before ovariectomy and 1 month after transplantation, in order to measure the delta of the tibias microarchitecture. (FIG. 6B) BV/TV, BV and TV were measured proximally in the trabecular bone of tibias. (FIG. 6C) the cortical bone volume and width were measured in the midshaft of the tibias. (FIG. 6D) Biomechanical analysis of the tibias using a 3-point bending test on mice as in FIG. 6A. The parameters measured include the yield point, the ultimate stress, the elastic energy, the energy to fracture and the Young's modulus. Data are displayed as mean±SD; n=8/group for the donors and n=10/group for the transplanted. Statistic are calculated based on Mann-Whitney t-test *>0.05, >0.01, *>0.001.

FIGS. 7A-C: *L. gasseri*, *L. reuteri* and heat-inactivaed (HI) *P. goldsteinii* can reduce or prevent bone fragility induce by ovariectomy. Ultimate strength (FIG. 7A) and post-yield displacement (FIG. 7B) measured by a 3-point bending biomechanical test on femur in ovariectomised mice supplemented with either *L. gasseri*, *L. Reuteri*, or HI *P. goldsteinii*. (FIG. 7C) Trabecular BV/TV measured by micro-CT in femur of the same mice.

DESCRIPTION OF ILLUSTRATIVE EMBODIMENTS

I. Definitions

Figures 1A, 1B, 1C, 1D, 1E, 1F, 1G:
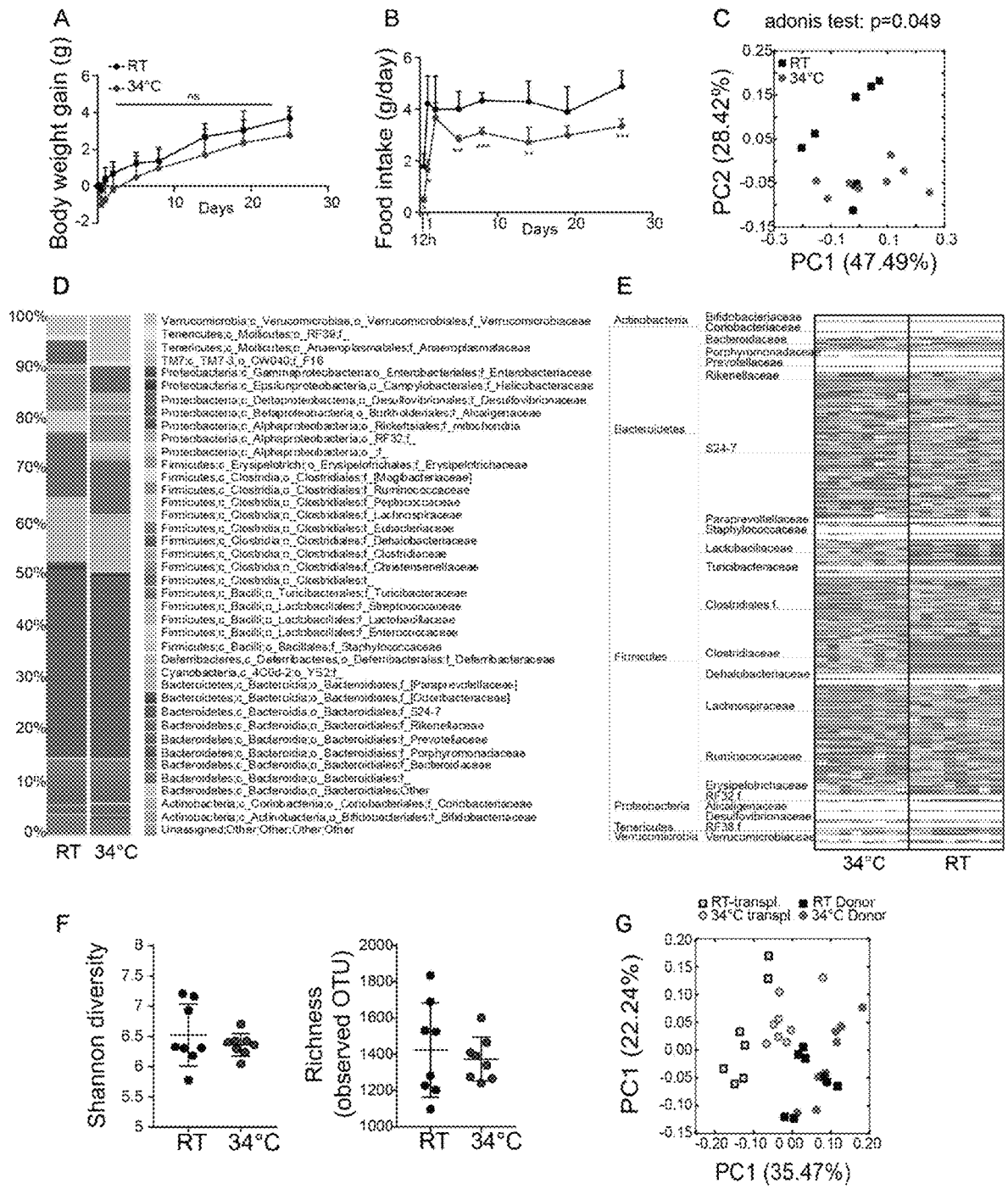
FIGS. 1A-1G show warm exposure changes in the gut microbiota population.

A "bacterial composition" is a composition that comprises one of more types of bacteria (e.g., live, dried, or heat-inactivated) or extracellular vesicles (i.e., secreted extracellular vesicles) from bacteria. In some embodiments, the bacteria are from the Clostridiaceae, Lactobacillaceae, and/or Porphyromonadaceae families. Specific bacteria that are contemplated include *Lactobacillus gasseri*, *Lactobacillus reuteri*, and *Parabacteroides goldsteinii* (e.g., live or heat-inactivated *P. goldsteinii*).

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a bacterial composition means that amount of the bacterial composition which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

As used herein, the term "patient" or "subject" refers to a living mammalian organism, such as a human, monkey, cow, sheep, goat, dog, cat, mouse, rat, guinea pig, or transgenic non-human species thereof. In certain embodiments, the patient or subject is a primate. Non-limiting examples of human patients are adults, juveniles, infants, and fetuses.

A "pharmaceutically acceptable carrier," "drug carrier," or simply "carrier" is a pharmaceutically acceptable substance formulated along with the active ingredient that is involved in carrying, delivering and/or transporting a biological agent. Carriers may be used to improve the delivery and the effectiveness of the active ingredient, including for example, controlled-release technology to modulate drug bioavailability, decrease drug metabolism, and/or reduce drug toxicity. Some carriers may increase the effectiveness of delivery of the active ingredient to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, hydrogels, starches, and dendrimers. In some embodiments, the carrier comprises an enteric coating (e.g., a fatty acid, a wax, a shellac, a plastic such as a phthalate, CAP, CAT, PVAP, HPMCP, or a plant fiber) to reduce or slow degradation in the stomach, chitosan-alginate beads, or a hydrogel.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

II. Warm Microbiota

As shown in the below examples, a variety of bacteria have been observed in warm microbiota, or the microbiota obtained from mammalian subjects living in warmer environments. These warm microbiota include *Clostridialeace-assimilate* spp., *Lactobacillus* spp. (e.g., *Lactobacillus gasseri* or *Lactobacillus reuteri*), *Bifidobacteriaceae* spp. (e.g., *Bifidobacterium longum*), *Parabacteroides* spp. (e.g., *Parabacteroides goldsteinii*) and *Akkermansia* spp. (e.g *Akkermansia muciniphila*). In some embodiments, it is anticipated that bacteria described in any one of Tables 1-5 may be included in a pharmaceutical composition or probiotic composition disclosed herein. In some embodiments, the pharmaceutical composition or probiotic composition may contain *Lactobacillus reuteri, Lactobacillus acidophilus,* and/or *Lactobacillus rhamnosus*. As shown in the examples, therapeutic responses may also be observed when using heat-inactivated *Parabacteroides goldsteinii*.

In various embodiments, it is anticipated that 1, 2, 3, 4, 5, 6, or more of the following types of bacteria may be included in a pharmaceutical composition or probiotic composition disclosed herein, e.g., as shown in any one of Tables 1-5. For example, the 1, 2, 3, 4, 5, 6, or more of *Clostridialeace-assimilate* spp., *Lactobacillus* spp. (e.g., *Lactobacillus reuteri, Lactobacillus gasseri, Lactobacillus acidophilus,* and/or *Lactobacillus rhamnosus*), *Bifidobacteriaceae* spp. (e.g., *Bifidobacterium longum*), *Parabacteroides* spp. (e.g., *Parabacteroides goldsteinii*) and *Akkermansia* spp. (e.g., *Akkermansia muciniphila*) may be included in a pharmaceutical or probiotic composition disclosed herein and/or administered to a mammalian subject, such as a human patient, to treat a bone disease. Various interactions between gut microbia and physiology may be used in combination with the present disclosure (e.g., as described in Ohlsson and Sjogren, 2015). *Lactobacillus* species such as *Lactobacillus reuteri* (Britton et al., 2014; also recently described in humans in Nilsson et al., 2018), *Lactobacillus acidophilus* (Dar et al., 2018), and/or *Lactobacillus rhamnosus* (Li et al., 2016) may be included in compositions for the treatment of a bone disease. In other embodiments, heat (e.g., from a heating chamber, heating pad, or a heating lamp) may be applied to the subject (e.g., to the whole body, or a specific zone, such as the torso, stomach, limbs, and/or abdomen) to treat a bone disease described herein, such as for example osteoporosis. In some embodiments, the heat applied may promote growth of warm microbiota.

III. Pharmaceutical Formulations and Routes of Administration

In another aspect, for administration to a patient in need of such treatment, pharmaceutical formulations (also referred to as bacterial formulations or pharmaceutical compositions) comprise a therapeutically effective amount of a bacterial composition disclosed herein formulated with one or more excipients and/or carriers appropriate to the indicated route of administration. In some embodiments, the bacteria disclosed herein are formulated in a manner amenable for the treatment of human and/or veterinary patients. In some embodiments, formulation comprises admixing or combining one or more of the bacteria disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the bacteria may be slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain carriers and/or excipients such as preservatives, stabilizers, wetting agents, emulsifiers, encapsulating agents such as lipids, dendrimers, polymers, proteins such as albumin, nucleic acids, and buffers.

Bacterial formulations may be administered by a variety of methods, e.g., orally, intracolonically, intranasally, intrarectally, via a catheter, via a lavage, via a nasogastric tube, via local delivery, or via a method for fecal microbiota transplantation (FMT). Depending on the route of administration, the bacterial compositions disclosed herein may be coated in a material to protect the bacterial compositions from the action of acids and other natural conditions which may inactivate the bacterial compositions. To administer the bacterial composition, it may be necessary to coat the bacterial composition with, or co-administer the bacterial composition with, a material to prevent its inactivation. In some embodiments, the bacterial composition may be administered to a patient in an appropriate carrier, for example, polymers, hydrogels, liposomes, starches, or a diluent. Pharmaceutically acceptable diluents include saline and aqueous buffer solutions. Liposomes include water-in-oil-in-water CGF emulsions as well as conventional liposomes.

Formulations may be employed to protect the bacterial compositions from the harsh gastric environment (Govander et al., 2014). Gastro-resistant polymers and coatings have been shown to supply protection against the harsh gastric environment. These coatings included enteric coated tablets and capsules that site-specifically deliver the administered probiotic bacteria to the intestinal system. These enteric coats are often pH selective and allow for protection against the harsh gastric conditions and subsequently dissolve in the alkali media of the intestinal system (Calinescu et al., 2005 and Yang et al., 2002). Non-limiting examples of excipients that may employed in the formulation of bacterial compositions are hydroxypropyl methylcellulose phthalate and carboxymethyl high amylose starch. Excipients may be combined to enhance delivery of the bacterial composition to the gastrointestinal tract. For example, carboxymethyl high amylose starch may be combined with chitosan for delivery of the bacterial composition to the colon. Formulations may include different polymers with different properties, or similar polymers with different properties, depending on the site of intended delivery to deliver the bacterial composition to different areas of the gastrointestinal tract (Yang et al., 2002).

The bacterial compositions disclosed herein may also be administered orally, intracolonically, intranasally, intrarectally, via a catheter, via a lavage, via a nasogastric tube, via local delivery, or via a method for fecal microbiota transplantation (FMT). The bacterial composition may be in the form of a dispersion. Dispersions can be prepared in glycerol, liquid polyethylene glycols, and mixtures thereof and in oils.

In some embodiments, the carrier comprises an enteric coating to reduce or slow degradation in the stomach. For example, the enteric coating may be a fatty acid, a wax, a shellac, a plastic such as a phthalate, CAP, CAT, PVAP, HPMCP, or a plant fiber (e.g., Hussan et al., 2012). In some embodiments, the pharmaceutical or probiotic composition may contain chitosan-alginate beads, or a hydrogel. Nonetheless, it is anticipated that in some embodiments, The bacterial compositions disclosed herein can be administered orally, for example, with an inert diluent or an assimilable edible carrier. The bacterial compositions and other ingredients may also be enclosed in a hard or soft-shell gelatin capsule, compressed into tablets, or incorporated directly into the patient's diet. For oral therapeutic administration, the bacterial compositions disclosed herein may be incorporated with excipients and used in the form of ingestible tablets, buccal tablets, troches, capsules, elixirs, suspensions, syrups, wafers, and the like. The percentage of the therapeutic agent in the compositions and preparations may, of course, be varied. The amount of the therapeutic agent in such pharmaceutical formulations is such that a suitable dosage will be obtained.

In some embodiments, it may be advantageous to formulate compositions in dosage unit form for ease of administration and uniformity of dosage. Dosage unit form as used herein refers to physically discrete units suited as unitary dosages for the patients to be treated; each unit containing a predetermined quantity of therapeutic agent calculated to produce the desired therapeutic effect in association with the required pharmaceutical carrier. In some embodiments, the specification for the dosage unit forms of the invention are dictated by and directly dependent on (a) the unique characteristics of the therapeutic agent and the particular therapeutic effect to be achieved, and (b) the limitations inherent in the art of compounding such a therapeutic agent for the treatment of a selected condition in a patient. In some embodiments, the active agent(s) are administered at a therapeutically effective dosage sufficient to treat a condition associated with a condition in a patient. For example, the efficacy of a bacterial composition can be evaluated in an animal model system that may be predictive of efficacy in treating the disease in a human or another animal.

In some embodiments, the effective dose range for the therapeutic agent can be extrapolated from effective doses determined in animal studies for a variety of different animals. Precise amounts of the therapeutic composition depend on the judgment of the practitioner and are specific to each individual. Other factors affecting the dose include the physical and clinical state of the patient, the route of administration, the intended goal of treatment and the potency, stability, and toxicity of the particular therapeutic formulation.

The actual dosage amount of a bacterial composition of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the patient has eaten or will eat.

IV. Extracellular Vesicles of Bacteria

In some embodiments, extracellular vesicles from bacteria described herein may be administered to a subject to treat a bone disorder. For examples, extracellular vesicles (EVs) may be produced via methods as described, for example, in Chelakkot et al., 2018, or Choi et al., 2015.

Extracellular vesicles (EVs) are lipid bilayer structures secreted from the gut microbiota, including from both Gram-negative and -positive bacteria (Ellis and Kuehn, 2010 and Lee et al., 2009). A variety of bacteria constitutively produce EVs, defined as spherical lipid bilayers with an average diameter of 20-200 nm (Lee et al., 2007). EVs are composed of proteins, lipids, nucleic acids, lipopolysaccharides and other virulence factors associated with pathogenesis (Horstman and Kuehn, 2002, Hong et al., 2011, and Kim et al., 2013). EVs released by bacteria may have diverse roles in the microbial community, and some data suggests that they may transfer genetic material and proteins from the bacteria to the host (Kuehn and Nesty, 2005). EVs may directly interact with immune cells and epithelial cells to initiate several signaling pathways and may affect or mediate host-pathogen interactions.

For example, in some embodiments, EVs may be prepared via the following approach. Bacterial species or warm microbiota may be cultured under aerobic or anaerobic conditions (e.g., 95% $N_2$ 5% $CO_2$ at 37° C.) until desired (e.g., when the optical density at 600 nm reaches 1.5, as previously described; Derrien et al., 2004). Isolation of EVs may be performed as previously described in Kang et al., 2013. More specifically, bacterial cultures may be pelleted at 10 000 g for 20 min, and the supernatant may then be filtered through a 0.45-µm vacuum filter. The filtrate can be enriched, e.g., using QuixStand (GE Healthcare, Little Chalfont, UK) and subsequently filtered through a 0.22-µm bottle-top filter. The filtrate may then be pelleted by ultracentrifugation (e.g., in a 45 Ti rotor at 150 000 g for 2 h at 4° C.). The final pellets may then be resuspended in phosphate-buffered saline (PBS) and stored at −80° C. EVs may be analyzed, if desired, by transmission electron microscopy, dynamic light scattering, and/or sodium dodecyl sulfate-polyacrylamide gel electrophoresis (SDS-PAGE) followed by gel staining with Coomassie Brilliant Blue R-250.

V. Bone Diseases

It is anticipated that a variety of bone diseases or disorders may be treated with the methods and bacterial compositions described herein. For example, a bacterial composition as described herein (e.g., live bacteria, heat inactivated bacteria, lyophilized bacteria, bacteria in a pharmaceutical composition, or secreted extracellular vesicles of the bacteria) may be administered enterically or to the gastrointestinal tract of a subject to treat a bone disease or disorder or promote or increase bone density. In some embodiments, the bone disease is osteoporosis, osteomalacia, periodontitis, rheumatoid arthritis, metabolic bone disease, a parathyroid disorder, steroid-induced osteoporosis, chemotherapy-induced bone loss, pre-menopausal bone loss, fragility and recurrent fractures, renal osteodystrophy, or Paget's disease. Without wishing to be bound by any theory, it is anticipated that the methods and bacterial compositions provided herein may be used to reduce cortical and/or trabecular bone loss, reduce cortical and/or trabecular bone mineral content loss, improve the bone biomechanical resistance, increase bone formation, and/or reduce bone-resorption.

In some embodiments, the disease is osteoporosis. Osteoporosis is the most prevalent of metabolic bone disorders, characterized by low bone mass and microarchitectural deterioration (Sozen et al., 2017). Patients with osteoporosis have fragile bones and are vulnerable to fractures. The most common type of primary osteoporosis is due to the postmenopausal estrogen deficiency, reflected in a higher incidence of osteoporosis in women (Reginster and Burlet, 2006).

VI. Temperature and Gut Microbiology

As shown herein, exposure to warm environments can change the microbiota of a mammalian subject, and the resulting "warm microbiota" has been shown herein to produce effects including increases in bone density that may be particularly beneficial for treating bone diseases such as osteoporosis. Some living organisms adapt to the perpetual change of their surrounding environment. One such external parameter is temperature, which can vary from below −35° C. to more than 40° C. and depends on seasonal periodicity and on the time of the day. Homeotherm animals need to conserve a constant body temperature; as a result, they have developed different strategies to adapt to these external fluctuations. In rodents, a thermogenic program is engaged upon cold stimulation, including shivering thermogenesis from the muscles and non-shivering thermogenesis from the adipose tissue. During warm exposure, in contrast, the thermogenic program is blunted and the energy expenditure reduced accordingly (Kaiyala et al., 2012). Additionally, to dissipate the heat excess, rodents increase skin vasodilation at specific locations where the surface to body ratio is high in order to maximize the heat loss. This is the case in the ears and tail (Meyer et al., 2017). Interestingly, scarce reports have suggested that upon longer exposure to elevated temperature, rodents adapt to maximize their ability to dissipate heat through an increase in their tail and ear length/surface (Alhilli and Wright, 1983, Ashoub, 1958, and Harland, 1960). This is associated with bone growth and has been reported to happen in the limbs in general, particularly described in the femur (Romsos et al., 1985 and Serrat et al., 2008). Unilateral heating of the limb from weaning time is associated with bone elongation and lengthening of the extremities on the heat exposed side only (Serrat et al., 2015). It has been postulated that the warm induced-vasodilatation, associated with an increased supply of nutrient and hormones could be the mediator of the bone elongation (Alhilli and Wright, 1983 and Ashoub, 1958). However, metatarsal growth in higher temperature was increased when the incubation was performed in vitro, thus independently of any vascularization and specific nutrient supply (Serrat et al., 2008). To date, there is no clear understanding on how the bone elongates under warm exposure and the actual evidences describing this phenomenon, and the mechanical properties of the bone remain poorly investigated.

The intestinal flora has been shown to affect some aspects of host physiology. Adaptation to cold exposure was shown to be partially mediated by the gut microbiota (Chevalier et al., 2015). The present disclosure shows that warm exposure can benefit bone characteristics (including length, microstructure, and mechanical resistance), and gut flora alterations play a role in these changes to bone characteristics. Thus, these beneficial effects may be utilized in the treatment of pathologic bone conditions, such as for example osteoporosis.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Results

Warm Exposure Changes Gut Microbiota Composition

To evaluate the effect of elevated external temperature on metabolism, 8-week old C57BL/6J male mice were exposed to 34° C. for one month and kept their controls at room temperature (RT, 22° C.). Warm exposure was initially associated with a slight decrease in body weight that was rapidly compensated to reach similar levels than the controls (FIG. 1A). Warm exposed mice decreased their food intake by about 25% for the whole course of the experiment and already 12 h after the start of the warm exposure (FIG. 1B). This decrease in food intake, despite the maintenance a normal body weight gain, has been described to be associated with a reduced energy expenditure (Abreu-Vieira et al., 2015), allowing mice to maintain the energy balance at equilibrium. To investigate if the gut microbiota is altered during warm, the 16S rDNA from fecal and cecal samples of animals exposed for one month to 34° C. and their RT controls were sequenced and the bacterial populations present in their gut microbiota were profiled. The relative distance between each microbiota was measured using principal coordinate analysis based on weighted Unifrac distance matrix (FIG. 1C). It was observed that the microbiota from 34° C.-exposed animals clustered differently from the RT ones. This was associated with a significant Adonis test with a p-value of 0.049. Although the difference in the general observed population is mild, several bacterial families were pointed to with different abundancies in 34° C.-exposed mice compared to RT (FIG. 1D and Table 1).

TABLE 1

Family abundance significant after Kruskal Wallis test (p < 0.05) in fecal sample of mice exposed 1 month at 34° C. and their RT controls. Among 49 identified genera, 11 had p < 0.05.

| Family | RT mean | Warm mean | median diff | log2 (medianFC) | P values |
|---|---|---|---|---|---|
| Firmicutes; Clostridia; Clostridiales; Clostridiaceae | 1.1E−03 | 1.7E−02 | 1.6E−02 | 4.1E+00 | 7.8E−04 |
| Firmicutes; Bacilli; Lactobacillales; Lactobacillaceae | 5.8E−03 | 2.0E−02 | 1.4E−02 | 1.9E+00 | 1.1E−03 |
| Bacteroidetes; Bacteroidia; Bacteroidales; Porphyromonadaceae | 3.3E−03 | 7.5E−03 | 4.0E−03 | 1.1E+00 | 1.6E−03 |
| Actinobacteria; Actinobacteria; Bifidobacteriales; Bifidobacteriaceae | 0.0E+00 | 1.5E−03 | 1.1E−04 | 2.0E+01 | 3.8E−03 |
| Firmicutes; Bacilli; Bacillales; Staphylococcaceae | 1.4E−06 | 2.5E−05 | 1.7E−05 | 1.7E+01 | 7.8E−03 |
| Firmicutes; Bacilli; Turicibacterales; Turicibacteraceae | 0.0E+00 | 3.0E−03 | 1.5E−03 | 2.4E+01 | 1.1E−02 |
| Firmicutes; Clostridia; Clostridiales; Peptostreptococcaceae | 0.0E+00 | 2.1E−05 | 2.3E−05 | 1.8E+01 | 1.1E−02 |
| Firmicutes; Erysipelotrichi; Erysipelotrichales; Erysipelotrichaceae | 9.5E−03 | 2.3E−02 | 1.5E−02 | 2.0E+00 | 1.6E−02 |
| Proteobacteria; Alphaproteobacteria; RF32; Other | 7.9E−03 | 1.8E−02 | 1.1E−02 | 1.9E+00 | 2.1E−02 |
| Actinobacteria; Coriobacteriia; Coriobacteriales; Coriobacteriaceae | 4.3E−04 | 1.9E−04 | −2.4E−04 | −1.3E+00 | 2.7E−02 |
| Proteobacteria; Alphaproteobacteria; Other; Other | 5.6E−04 | 1.1E−03 | 7.7E−04 | 1.9E+00 | 2.7E−02 |

Among 49 identified families, 11 were significantly differentially abundant in feces. This was the case of the Clostridiaceae, the Lactobacillaceae and the Porphyromonadaceae families that were the most significantly increased after warm exposure with an abundance higher than 0.5% on average. It was also noticed that Verrucomicrobiaceae were increased after warm exposure to range around 10% of mean abundance, despite not reaching statistical significance due to high variability (p=0.09). Within the significantly altered families (p>0.05), the associated heatmap representing OTUs (operational taxonomic units) belonging to each family showed that all the OTUs present in the three previously mentioned families were increased after warm exposure (FIG. 1E and Table 1). At the genera level, *Lactobacillus*, an unidentified genus of *Clostridiaceae*, and *Parabacteroides* were the three most significantly increased after warm exposure, thus confirming the previous observation since they are part of the families Clostridiaceae, Lactobacillaceae, and Porphyromonadaceae respectively (Table 2).

TABLE 2

OTUs filter for a p-value <0.05 (Kruskal-Wallis test), a median difference > 0.003 and a $\log^2$ median fold change > 1, in fecal samples of mice exposed 1 month at 34° C. and their RT controls. Among 1698 identified OTU, 21 were corresponding to the criteria above, and 272 had p < 0.05.

| OTU ID | Taxonomy | | | |
|---|---|---|---|---|
| | Phylum | Class | Order | Family |
| 224155 | Firmicutes | Clostridia | Clostridiales | Clostridiaceae |
| 392918 | Firmicutes | Clostridia | Clostridiales | Ruminococcaceae |
| 780650 | Firmicutes | Clostridia | Clostridiales | Clostridiaceae |
| 555945 | Firmicutes | Clostridia | Clostridiales | Clostridiaceae |
| 460953 | Bacteroidetes | Bacteroidia | Bacteroidales | S24-7 |
| 216524 | Bacteroidetes | Bacteroidia | Bacteroidales | S24-7 |
| 268352 | Firmicutes | Erysipelotrichi | Erysipelotrichales | Erysipelotrichaceae |
| 4426641 | Firmicutes | Erysipelotrichi | Erysipelotrichales | Erysipelotrichaceae |
| 592160 | Firmicutes | Bacilli | Lactobacillales | Lactobacillaceae |
| 588197 | Firmicutes | Bacilli | Lactobacillales | Lactobacillaceae |
| 290338 | Firmicutes | Clostridia | Clostridiales | nd |
| New.RefOTU10886 | Proteobacteria | Alphaproteobacteria | RF32 | nd |
| 589071 | Bacteroidetes | Bacteroidia | Bacteroidales | Bacteroidaceae |
| 276149 | Bacteroidetes | Bacteroidia | Bacteroidales | Porphyromonadaceae |
| 339905 | Bacteroidetes | Bacteroidia | Bacteroidales | S24-7 |
| 331720 | Bacteroidetes | Bacteroidia | Bacteroidales | S24-7 |
| 228601 | Bacteroidetes | Bacteroidia | Bacteroidales | Bacteroidaceae |
| 348038 | Bacteroidetes | Bacteroidia | Bacteroidales | S24-7 |
| 346870 | Bacteroidetes | Bacteroidia | Bacteroidales | S24-7 |
| 228730 | Bacteroidetes | Bacteroidia | Bacteroidales | S24-7 |
| 264657 | Bacteroidetes | Bacteroidia | Bacteroidales | S24-7 |

| OTU ID | Taxonomy | | RT mean | Warm mean | Log2 median FC | median diff. | P values |
|---|---|---|---|---|---|---|---|
| | Genus | Species | | | | | |
| 224155 | nd | nd | 1.4E−06 | 6.9E−03 | 3.0E+01 | 8.1E−03 | 4.5E−04 |
| 392918 | nd | nd | 2.1E−06 | 9.9E−03 | 2.9E+01 | 7.0E−03 | 4.5E−04 |
| 780650 | nd | nd | 2.6E−06 | 3.3E−03 | 2.9E+01 | 4.1E−03 | 4.5E−04 |
| 555945 | nd | nd | 0.0E+00 | 3.5E−03 | 2.8E+01 | 3.6E−03 | 3.3E−04 |
| 460953 | nd | nd | 4.0E−03 | 2.1E−02 | 3.6E+00 | 1.9E−02 | 7.8E−04 |
| 216524 | nd | nd | 5.7E−03 | 5.5E−02 | 3.6E+00 | 5.1E−02 | 7.8E−04 |
| 268352 | Allobaculum | nd | 2.1E−03 | 9.9E−03 | 3.5E+00 | 6.8E−03 | 1.6E−03 |
| 4426641 | Allobaculum | nd | 1.7E−03 | 7.7E−03 | 3.2E+00 | 6.0E−03 | 1.1E−03 |
| 592160 | Lactobacillus | nd | 2.9E−03 | 1.4E−02 | 2.5E+00 | 1.1E−02 | 1.1E−03 |
| 588197 | Lactobacillus | nd | 1.4E−03 | 3.8E−03 | 2.4E+00 | 3.4E−03 | 3.3E−03 |
| 290338 | nd | nd | 2.2E−03 | 6.2E−03 | 2.4E+00 | 3.3E−03 | 4.6E−02 |
| New.RefOTU10886 | nd | nd | 7.8E−03 | 1.7E−02 | 1.9E+00 | 1.1E−02 | 2.1E−02 |
| 589071 | Bacteroides | nd | 2.4E−03 | 5.4E−03 | 1.5E+00 | 3.5E−03 | 2.7E−02 |
| 276149 | Parabacteroides | nd | 3.2E−03 | 7.4E−03 | 1.2E+00 | 4.0E−03 | 1.6E−03 |
| 339905 | nd | nd | 1.3E−02 | 6.7E−03 | −1.1E+00 | −7.4E−03 | 1.6E−02 |
| 331720 | nd | nd | 2.7E−02 | 1.0E−02 | −1.1E+00 | −1.2E−02 | 7.8E−04 |
| 228601 | Bacteroides | nd | 1.5E−02 | 7.2E−03 | −1.2E+00 | −7.9E−03 | 1.2E−02 |
| 348038 | nd | nd | 7.3E−03 | 4.0E−03 | −1.3E+00 | −4.8E−03 | 8.7E−03 |
| 346870 | nd | nd | 2.3E−02 | 9.3E−03 | −1.5E+00 | −1.5E−02 | 1.1E−03 |
| 228730 | nd | nd | 1.4E−02 | 5.2E−03 | −1.5E+00 | −1.0E−02 | 2.3E−03 |
| 264657 | nd | nd | 4.9E−03 | 1.6E−03 | −1.5E+00 | −3.1E−03 | 1.6E−03 |

Looking at the OTU level (Table 3), the same families and genera were highlighted with several OTUs from Clostridiaceae family, two OTUs from *Lactobacillus* genus and one OTU from *Parabacteroides*. Other OTUs from S24-7 family and *Allobaculum* genus were also part of the most differently abundant OTUs. Elevated temperature exposure had no effect on the richness or diversity of the gut microbiota (FIG. 1F).

TABLE 3

Genera abundance significant after Kruskal Wallis test (p < 0.05) in fecal samples of mice exposed 1 month at 34° C. and their RT controls. Among 73 identified genera, 13 had p < 0.05.

| Genera | RT mean | 34° C. mean | median diff | log2 (medianFC) | P values |
|---|---|---|---|---|---|
| Firmicutes; Clostridia; Clostridiales; Clostridiaceae; Other | 7.5E−04 | 1.6E−02 | 1.5E−02 | 4.4E+00 | 7.8E−04 |
| Firmicutes; Bacilli; Lactobacillales; Lactobacillaceae; *Lactobacillus* | 5.8E−03 | 2.0E−02 | 1.4E−02 | 1.9E+00 | 1.1E−03 |
| Bacteroidetes; Bacteroidia; Bacteroidales; Porphyromonadaceae; *Parabacteroides* | 3.3E−03 | 7.5E−03 | 4.0E−03 | 1.1E+00 | 1.6E−03 |
| Actinobacteria; Actinobacteria; Bifidobacteriales; Bifidobacteriaceae; *Bifidobacterium* | 0.0E+00 | 1.5E−03 | 1.1E−04 | 2.0E+01 | 3.8E−03 |
| Firmicutes; Bacilli; Bacillales; Staphylococcaceae; *Staphylococcus* | 1.4E−06 | 2.5E−05 | 1.7E−05 | 1.7E+01 | 7.8E−03 |
| Firmicutes; Erysipelotrichi; Erysipelotrichales; Erysipelotrichaceae; *Allobaculum* | 6.2E−03 | 1.9E−02 | 1.3E−02 | 2.9E+00 | 8.7E−03 |
| Firmicutes; Bacilli; Turicibacterales; Turicibacteraceae; *Turicibacter* | 0.0E+00 | 3.0E−03 | 1.5E−03 | 2.4E+01 | 1.1E−02 |

TABLE 3-continued

Genera abundance significant after Kruskal Wallis test (p < 0.05) in fecal samples of mice
exposed 1 month at 34° C. and their RT controls. Among 73 identified genera, 13 had p < 0.05.

| Genera | RT mean | 34° C. mean | median diff | log2 (medianFC) | P values |
|---|---|---|---|---|---|
| Firmicutes; Clostridia; Clostridiales; Clostridiaceae; SMB53 | 0.0E+00 | 3.2E−05 | 1.7E−05 | 1.7E+01 | 1.1E−02 |
| Firmicutes; Clostridia; Clostridiales; Peptostreptococcaceae; Other | 0.0E+00 | 2.1E−05 | 2.3E−05 | 1.8E+01 | 1.1E−02 |
| Proteobacteria; Alphaproteobacteria; RF32; Other; Other | 7.9E−03 | 1.8E−02 | 1.1E−02 | 1.9E+00 | 2.1E−02 |
| Firmicutes; Clostridia; Clostridiales; Lachnospiraceae; Other | 3.4E−02 | 1.3E−02 | −9.3E−03 | −9.4E−01 | 2.7E−02 |
| Proteobacteria; Alphaproteobacteria; Other; Other; Other | 5.6E−04 | 1.1E−03 | 7.7E−04 | 1.9E+00 | 2.7E−02 |
| Firmicutes; Clostridia; Clostridiales; Clostridiaceae; *Candidatus Arthromitus* | 1.5E−04 | 3.9E−04 | 2.2E−04 | 2.1E+01 | 4.3E−02 |

While analysis of the cecal microbiota (Table 4) showed fewer differences between warm and RT mice compared to the fecal microbiota, increased *Lactobacillus* abundance was a similar hallmark in both microbiota specimens. Taken together, these results show that warm exposure in mice changes the gut microbiota composition with a particular increase in the genera *Lactobacillus, Clostridiaceae*-assimilate and *Parabacteroides* in feces.

TABLE 4

Significant differentially abundant genera of cecal samples of mice exposed 1 month at 34° C.
and their RT controls (p < 0.05 after Kruskal-Wallis test). Among 64 identified genera, 5 had p < 0.05.

| Genera cecum | RT mean | Warm mean | median diff | log2 (medianFC) | P values |
|---|---|---|---|---|---|
| Firmicutes; Bacilli; Lactobacillales; Lactobacillaceae; *Lactobacillus* | 0.0036 | 0.0084 | 0.0036 | 0.9005 | 0.0087 |
| Tenericutes; Mollicutes; Anaeroplasmatales; Anaeroplasmataceae; *Anaeroplasma* | 0.0003 | 0.0085 | 0.0043 | 5.6683 | 0.0180 |
| Firmicutes; Bacilli; Turicibacterales; Turicibacteraceae; *Turicibacter* | 0.0000 | 0.0060 | 0.0005 | 22.1440 | 0.0273 |
| Firmicutes; Clostridia; Clostridiales; Lachnospiraceae; *Coprococcus* | 0.0057 | 0.0031 | −0.0008 | −0.2948 | 0.0274 |
| Firmicutes; Clostridia; Clostridiales; Lachnospiraceae; Other | 0.0681 | 0.0408 | −0.0113 | −0.3554 | 0.0460 |

Gut Microbiota Contributes to the Thermogenic Adaptation to Warm

To evaluate the effect of the gut microbiota on the warm ambient temperature adaptation, germ-free (GF) mice were transplanted with 'warm' cecal microbiota (warm-transplanted) (FIG. 1C-1F and Tables 1-4) and were compared to RT microbiota-transplanted GF (RT-transplanted) control mice. All transplanted mice were maintained at RT. The transplantation efficiency was confirmed using principal coordinate analysis (FIG. 1G), where the transplanted recipients showed similar changes to their donors. The difference in the transplanted animals' microbiota compared with Adonis test was significant with a p-value of 0.01. In addition, similar bacterial hits to the donors were found in the transplanted microbiota as the most differentially abundant family, such as Clostridiaceae (here associated to *Clostridium*), *Parabacteroides*, and *Akkermansia, Lactobacillus*, however, was not increased in the warm transplanted animals, likely due to a disadvantageous competition post-transplantation.

TABLE 5

Differentially abundant genera in fecal microbiota of RT- and warm-transplanted mice (Kruskal Wallis test p < 0.05).

| genera | P value | 34° C. transpl. mean | RT transpl. mean |
|---|---|---|---|
| Firmicutes; Clostridia; Clostridiales; Clostridiaceae; *Clostridium* | 5.60E−04 | 5.30E−06 | 1.40E−04 |
| Firmicutes; Clostridia; Clostridiales; Lachnospiraceae; *Dorea* | 1.60E−03 | 3.90E−04 | 6.10E−05 |
| Verrucomicrobia; Verrucomicrobiae; Verrucomicrobiales; Verrucomicrobiaceae; *Akkermansia* | 1.60E−03 | 8.30E−02 | 1.20E−02 |
| Bacteroidetes; Bacteroidia; Bacteroidales; Porphyromonadaceae; *Parabacteroides* | 4.60E−03 | 5.80E−03 | 3.20E−03 |
| Bacteroidetes; Bacteroidia; Bacteroidales; Rikenellaceae; other | 4.60E−03 | 1.00E−01 | 1.70E−01 |
| Bacteroidetes; Bacteroidia; Bacteroidales; [Odoribacteraceae]; *Odoribacter* | 4.60E−03 | 2.10E−03 | 8.40E−03 |

TABLE 5-continued

Differentially abundant genera in fecal microbiota of RT- and warm-transplanted mice (Kruskal Wallis test p < 0.05).

| genera | P value | 34° C. transpl. mean | RT transpl. mean |
|---|---|---|---|
| Tenericutes; Mollicutes; Anaeroplasmatales; Anaeroplasmataceae; *Anaeroplasma* | 8.60E−03 | 3.20E−04 | 3.20E−03 |
| Bacteroidetes; Bacteroidia; Bacteroidales; other; other | 8.70E−03 | 1.10E−02 | 2.40E−02 |
| Firmicutes; Clostridia; Clostridiales; Lachnospiraceae; Other | 8.70E−03 | 4.30E−04 | 2.20E−03 |
| Firmicutes; Clostridia; Clostridiales; Lachnospiraceae; *Blautia* | 1.50E−02 | 6.80E−05 | 1.70E−05 |
| TM7; TM7-3; CW040; F16; other | 2.00E−02 | 1.00E−05 | 4.70E−05 |
| ActinoCoriobacteriia; Coriobacteriales; Coriobacteriaceae; other | 4.30E−02 | 8.30E−05 | 2.00E−05 |
| Firmicutes; Clostridia; Clostridiales; Other; Other | 4.60E−02 | 4.60E−03 | 1.40E−03 |

Figures 2A, 2S:
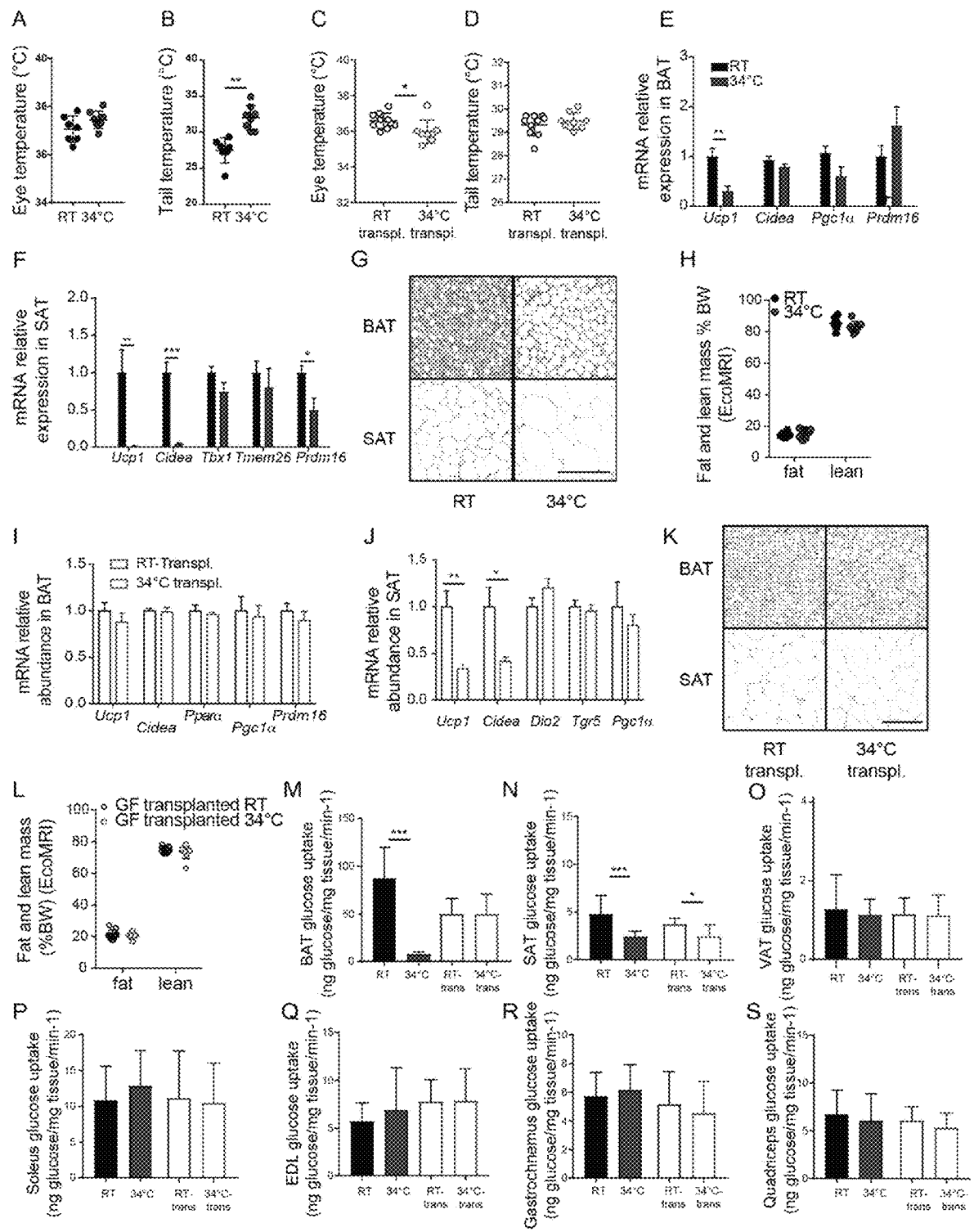
FIGS. 2A-2S show warm exposure leads to whitening of the adipose tissue, and this is partially mediated by the microbiota.

Under warm temperature, mice need to maintain a constant body temperature around 37° C. This is enabled by blunting the thermogenic program and increasing the vasodilatation of the tail (and ears) to dissipate the excessive heat (Kaiyala et al., 2012, Alhilli and Wright, 1983, Ashoub, 1958, and Harland, 1960). In the experimental setting, mice exposed one month at 34° C. were able to maintain their body temperature constant (reflected by the eye temperature) (FIG. 2A), mediated by an increased temperature dissipation through their tail (FIG. 2B). To understand if the gut microbiota composition could participate in the adaptation to warm exposure, the same parameters were measured in the mice transplanted with the microbiota of warm exposed mice (warm-transplanted). Surprisingly, the mice receiving the warm microbiota had a slight decrease in their eye temperature, representative of their body temperature (FIG. 2C). This suggests that the warm microbiota alone is sufficient to decrease the core body temperature. This lower temperature was not mediated by an increased heat dissipation from the tail, as no differences in the tail temperature between the warm- and RT-transplanted mice was noticed (FIG. 2D). This suggests that other thermoregulatory mechanisms have been transplanted through the microbiota in these mice. Cold environment stimulates a thermogenic response to maintain body temperature at a constant level, it initiates shivering thermogenesis through muscular contraction and non-shivering thermogenesis with brown or beige adipose tissue activation. The main effector protein is the uncoupling protein 1 (UCP1) that uncouples the oxidative phosphorylation in the mitochondria from the ATP production and alleviates heat production. In the context of warm exposure, this phenomenon is blunted and the activity of brown and beige adipose tissue is reduced (Cui et al., 2016). This was confirmed in the experimental setting where Ucp1 and other thermogenic markers expression level were reduced both in the interscapular brown adipose tissue (BAT; FIG. 2E) and in subcutaneous adipose tissue (SAT; FIG. 2F). In addition, the morphology of this tissue changed to an increased lipid droplet size and disappearance of the multilocular cells (numerous small lipid droplets normally present in the active brown or beige adipocytes; FIG. 2G). This was associated with a maintenance of the fat mass despite the reduced food intake (FIG. 1B and FIG. 2H). It was suspected that the reduced basal body temperature of the warm transplanted mice was also due to an effect of the microbiota on the adipose tissue thermogenic activity. While changes in thermogenic genes expression in the BAT were not observed (FIG. 2I), Ucp1 and Cidea showed reduced expression in the SAT indicating a whitening of the adipose tissue (FIG. 2J). Neither morphological changes in the H&E stained sections of the BAT and SAT of the transplanted mice, nor any repercussion on fat mass distribution (FIGS. 2K-2L) were detected. In contrast, the decreased thermogenic genes expression was reflected in the glucose uptake of the tissues. Specifically, it was observed a reduced glucose uptake in BAT and SAT of the warm exposed animals that was also present in SAT of warm microbiota-transplanted mice (FIGS. 2M-2N). No changes were observed in visceral adipose tissue (VAT) and muscles glucose uptake (FIGS. 2O-2S), confirming the specific decreased glucose uptake mediated by decreased thermogenic activity. This suggests that mice adapt to warm temperature by altering their thermogenic activity, partially through a gut microbiota adaptation.

Bone Morphology Adaptation After Warm Exposure

Figures 3A, 3B, 3C, 3D, 3E, 3F, 3G, 3H, 3I, 3J, 3K:
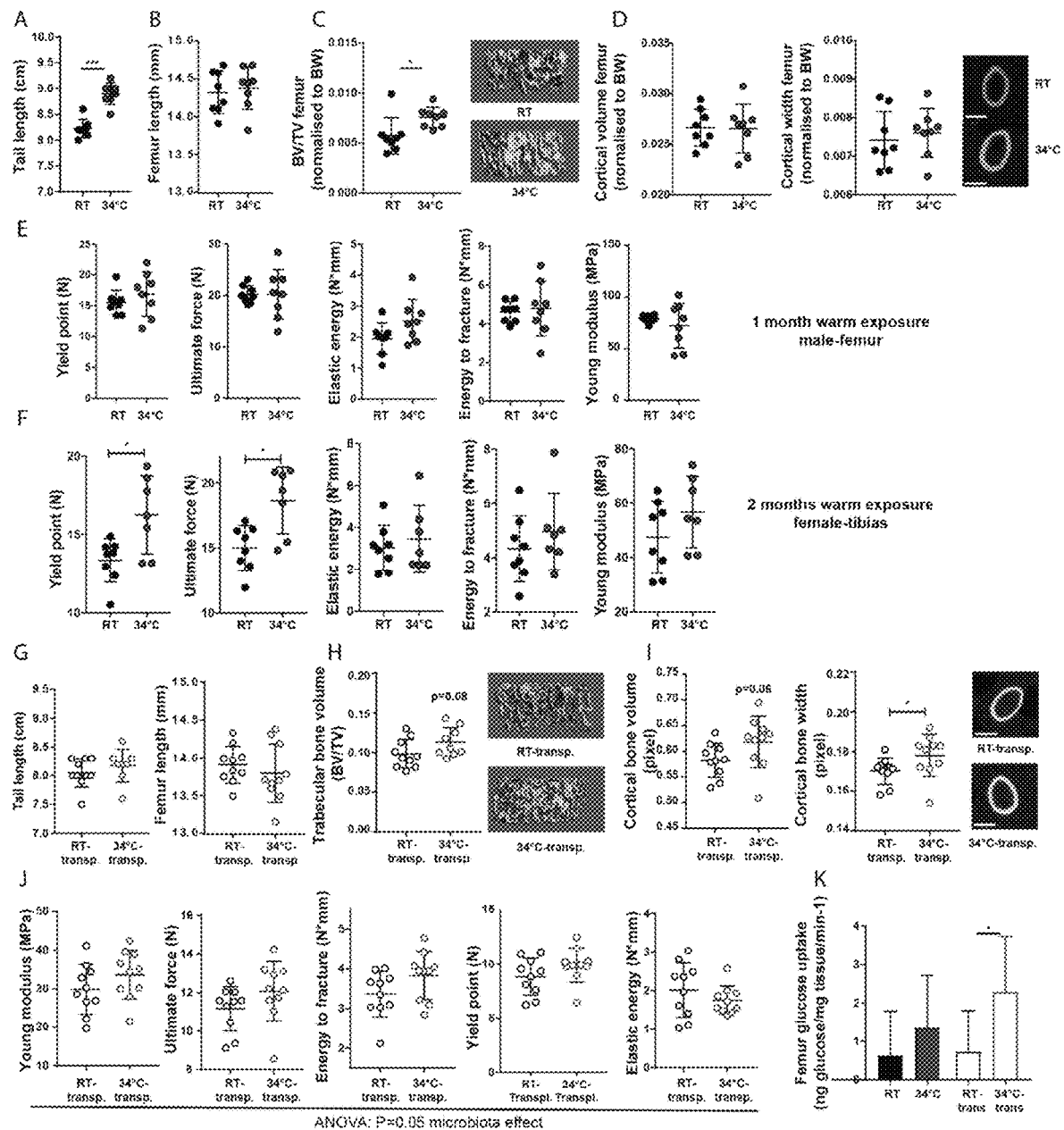
FIGS. 3A-3K show warm exposure and warm microbiota transplantation are associated with increased bone strength.
Figures 4A, 4B, 4C, 4D, 4E, 4F, 4G, 4H, 4I, 4J, 4K:
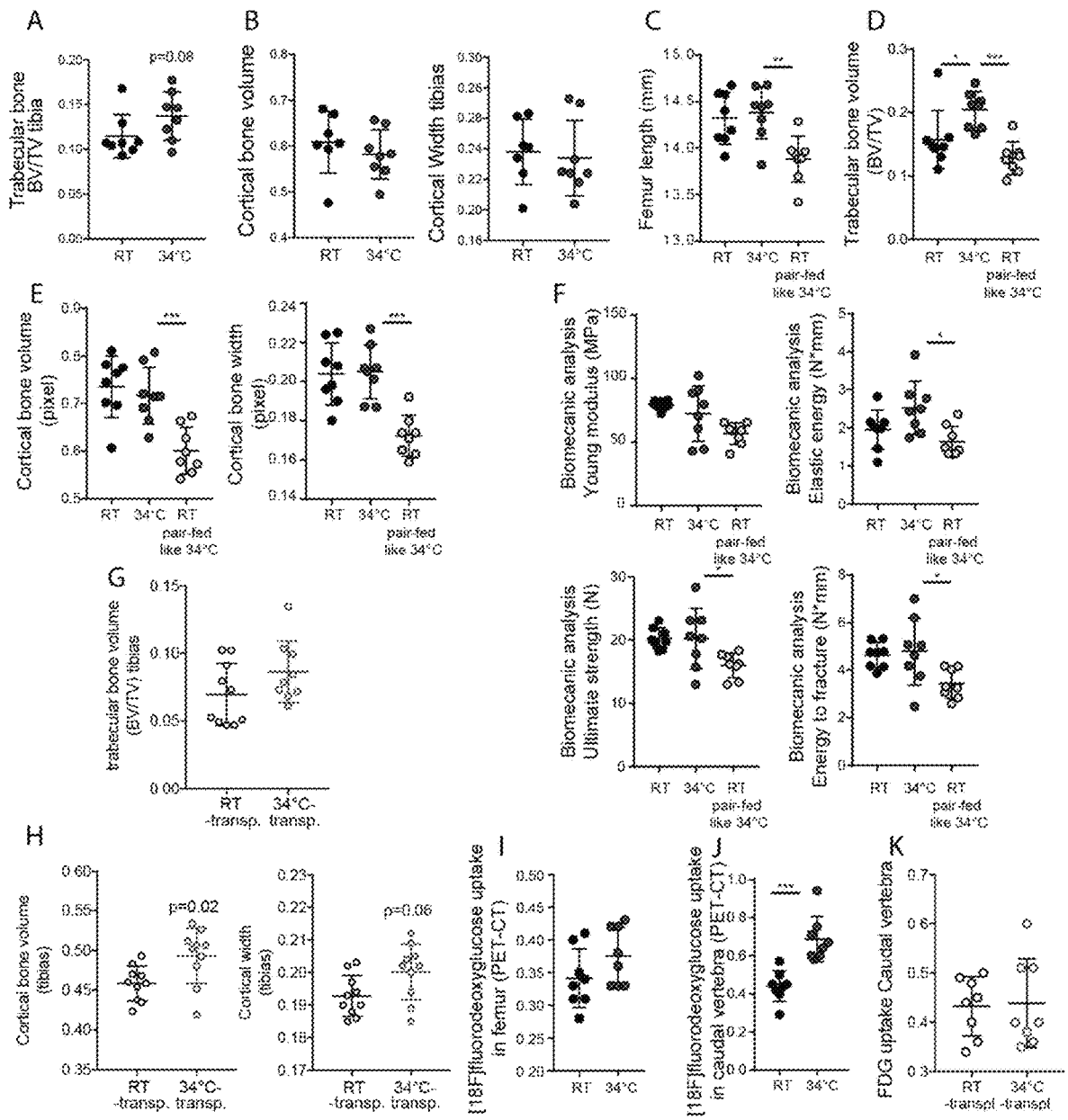
FIGS. 4A-4K show bone characteristics as a result of exposure to warm as well as bone characteristics as a result of transplantation of microbiota from warm-exposed mice. (FIG. A) Bone volume density (BV/TV), measured proximally in the trabecular bone of the tibias, in mice as in the FIG. 3C.

Heat dissipation in rodents is mediated by vasodilatation of the extremities, mainly in the tail. This phenomenon is associated with an increase in the tail and ear length to maximise the surface ratio for heat dissipation (Serrat et al., 2008). In the experimental setting, this observation was confirmed as after one month of warm exposure the tail length increased by 8% relative to the controls (~0.7 cm longer) (FIG. 3A). It was further analysed whether warm exposure had an effect on long bone growth, and examined the structure of the femur. Serrat and coworkers showed that warm exposure from weaning to adulthood was leading to tail elongation, but also limbs like in the femur (Serrat et al., 2008). Although there was no difference in total femur length between mice exposed one month to warm and their RT controls (FIG. 3B), the structural analysis of the femur by micro-CT showed morphological changes. The trabecular bone proportion increased as reflected by the bone volume (BV)/total volume (TV) ratio (FIG. 3C), but no differences in the cortical bone were found (FIG. 3D). Similar structural changes as in the femur were observed in the tibia (FIGS. 4A & 4B). To investigate if these morphological changes were reflected in the biomechanical resistance of the bone, a three-point bending test was performed on the femur. Despite the trabecular increase in BV/TV ratio, no changes in the mechanical strength were observed (FIG. 3E). However, when the same test was performed on older female mice exposed longer to 34° C. (two months), it was observed that both the yield point and the ultimate force were significantly increased with warm exposure (FIG. 3F). This suggests that long-term warm exposure has an impact on the bone morphology and associated strength, although age and sex dimorphism may interfere in the bone morphology in response to temperature. It has been previously shown that caloric restriction impaired bone mass both in rodent models and in humans (Devlin et al., 2010, Legroux-Gerot et al., 2007, Villareal et al., 2006, and Sanderson et al., 1997). As mentioned above, warm exposure is associated with a reduction in food intake of ~25% (FIG. 1B). To control for this reduced food intake, the same experiment was performed with an additional group of mice that were pair-fed like the warm exposed mice (25% less food than the RT controls) but kept at RT. It was observed that despite their reduced food intake, the warm exposed mice were able to maintain the structure and the biomechanical strength of the femur, while the pair-fed mice displayed a reduced trabecular and cortical bone density as well as a mechanical fragility of the femur (FIGS. 4C-4F). This is in line with the beneficial effect of warm exposure on the bone strength, even if the comparison with pair-fed mice implies other regulatory mechanisms (especially regarding the energy balance of the two groups). It was then investigated if this adaptation could be mediated by the gut microbiota and measured the same parameter in the transplanted animals. Although differences in the total tail and femur lengths were not detected (FIG. 3G), the structural parameters of the femur were improved with warm microbiota transplantation. There was a tendency for higher trabecular BV/TV ratio (FIG. 3H), while at a cortical level, both the cortical bone volume and width in the femur (FIG. 3I) and in the tibias (FIGS. 4G & 4H) were increased with warm-microbiota transplantation. This suggests an impact of the gut microbiota to maintain bone mass at both the trabecular and cortical levels. To follow up on the structural changes of the bone, biomechanical analysis was performed and it was observed that all parameters measuring the strength of the bone were increased with warm microbiota transplantation. ANOVA analysis of all the biomechanical parameters revealed that the microbiota-induced changes were significant ($p=0.05$). Of note, these effects were measured only after 20 days of transplantation. Since the bone remodeling is very energy demanding, the glucose uptake in the femur and the caudal vertebra was measured and it was observed that glucose uptake was increased both in warm exposed animals and in warm-microbiota transplanted ones, in line with the structural and mechanical measurements (FIG. 3K and FIGS. 4I-4K). Taken together, this suggests that warm exposure has a positive effect on bone density and strength already after one month of warm exposure and the effect is amplified after two months. This is in part mediated by a shift in the gut microbiota population, which induces structural and mechanical changes already after 20 days of transplantation.

Effect of Warm Exposure on Osteoporosis

Figures 5A, 5B, 5C, 5D, 5E, 5F, 5G, 5H, 5I:
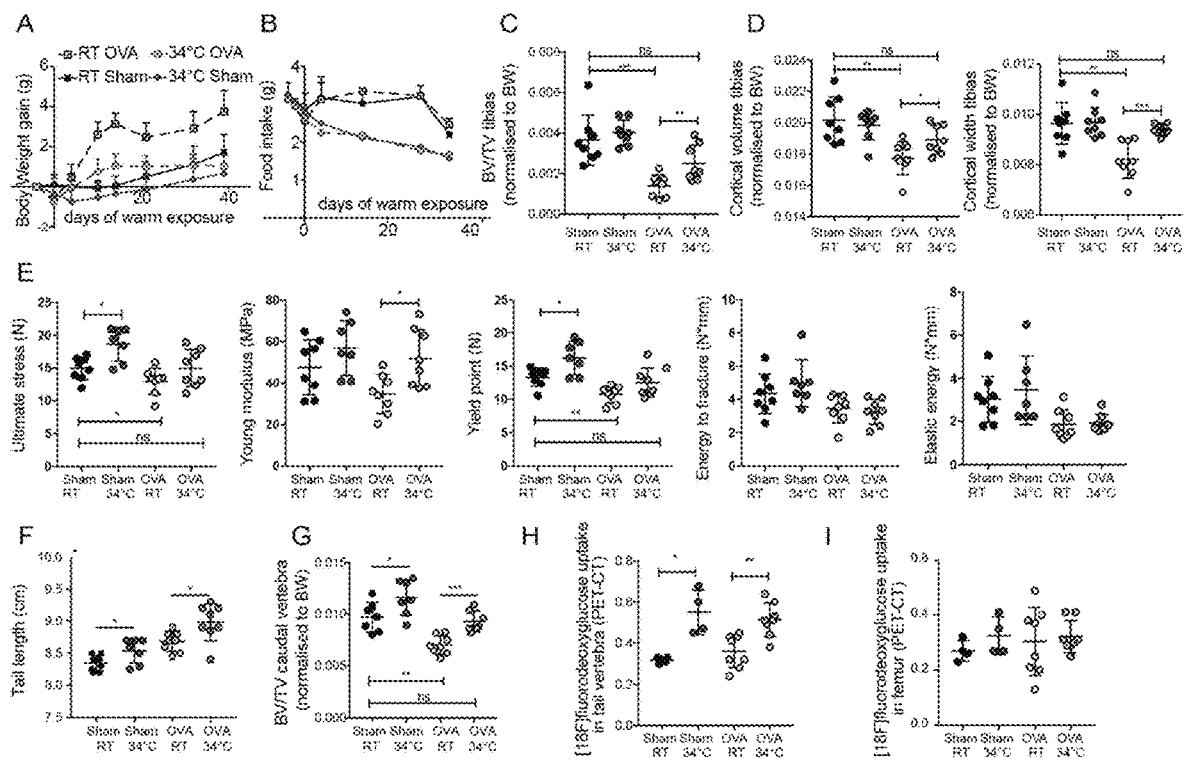
FIGS. 5A-5I show warm exposure prevents osteoporosis-induced bone loss in ovariectomized mice.

Next, it was investigated whether the positive effect of warm exposure on the bone morphology could lead to improvement in a pathological context. Osteoporosis is caused by an imbalance between the bone formation and the bone resorption and is a leading cause of fractures in aged individuals. One of the main factors associated with osteoporosis is oestrogen deficiency present during the post-menopausal period in women. To evaluate if warm exposure could have a positive effect on osteoporosis, aged ovariectomized mice were used that mimic the post-menopausal osteoporosis observed in humans. Four groups of mice were used: two groups were sham operated as controls (one kept two months at 34° C., and the other at RT) and two groups were ovariectomized (similarly kept either at 34° C. or at RT). Consistent with previous observations (Iwasa et al., 2018), the ovariectomized mice gained more weight than their sham-operated controls. Surprisingly, warm exposure was sufficient to prevent this body weight gain, and the mice were able to maintain a body weight similar to the sham-operated ones (FIG. 5A) coupled with 25% reduction in the food intake (FIG. 5B). Body weight and the associated mechanical load put on the bone has an effect on the bone density and strength (Iwaniec and Turner, 2016). To exclude this confounding factor, the next results were normalized to the body weight of the mice. As expected, the structure of the trabecular bone (BV/TV) and the cortical bone (volume and width) were decreased after ovariectomy. This was, however, prevented by warm exposure, where all the parameters were close to the sham-operated animals (FIGS. 5C & 5D). Differences observed in ovariectomized mice after warm exposure were more exacerbated than in sham-operated mice. This suggests that the mechanisms involved in bone deterioration due to oestrogen deficiency can be prevented by mechanisms deployed during warm exposure. Interestingly, the rescue observed at the structural level was also reflected at the mechanical level. While energy to fracture and elastic energy were not affected, the ultimate force the bone can endure before breaking was improved in ovariectomized mice after warm exposure (compared to the RT-kept mice). Parameters assessing the flexible part of the bone like the young modulus and the yield point were also improved, reaching similar levels as the control sham-operated mice (FIG. 5E). This suggests that warm exposure can prevent ovariectomy-induced osteoporosis. Additionally, the effect on the tail elongation normally present after warm exposure was conserved despite ovariectomy (FIG. 5F). The structure of the tail vertebra was also affected, with the same pattern as for the tibias (FIG. 5G), indicating a broad beneficial effect of the warmth on osteoporosis in long bones and in vertebras. It was also noticed that despite ovariectomy, warm exposure was accompanied by an increased glucose uptake in caudal vertebra (FIG. 5H), indicating an increase in their metabolic activity. However, the glucose uptake in the femur was similar in both warm-ovariectomized and RT-ovariectomized, probably due to the basal increased remodeling activity present in osteoporosis (FIG. 5I).

Effect of Warm Microbiota on Osteoporosis

Figures 6A, 6B, 6C, 6D:
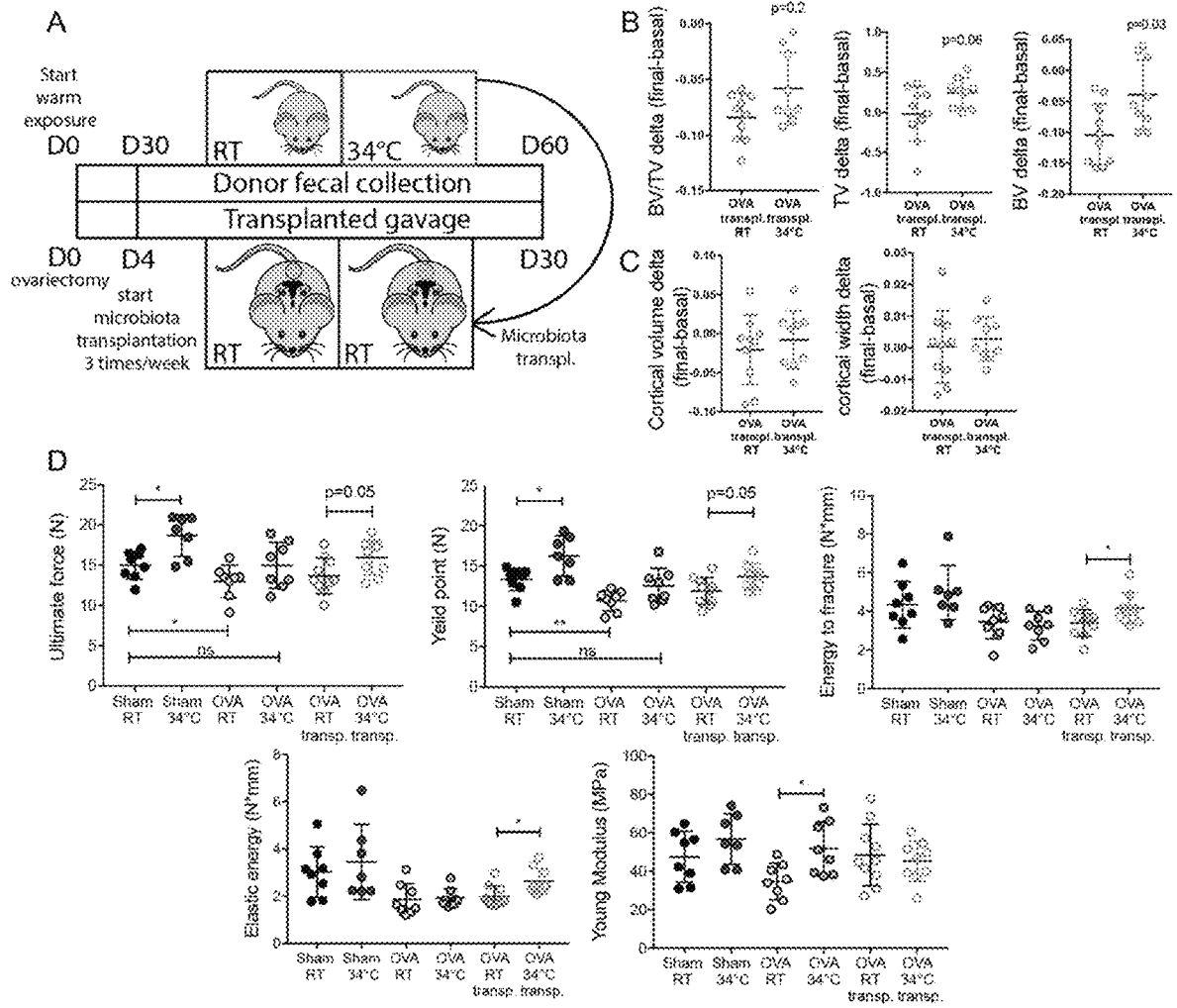
FIGS. 6A-6D show warm microbiota transplantation to ovariectomized mice prevents osteoporosis-associated bone fragility.

It was wondered whether the prevention of osteoporosis observed with warm exposure can be also achieved by transplantation of the warm-adapted microbiota. To investigate this, an experiment was designed wherein donor mice previously exposed for one month at 34° C. or RT were maintained to freshly transplant their fecal microbiota. Recipient mice were ovariectomized and transplanted with the donor microbiota every second day for one month (FIG. 6A). In this cohort, the tibia structure was measured before and one month after the ovariectomy. This allowed for the calculation of the change (delta) in the bone microarchitecture before and after the treatment to measure the effect of transplantation on the osteoporosis outcome. The trabecular BV/TV was slightly increased, but not significantly. This was the consequence of a double effect of the temperature, increasing both the bone volume (BV) and the total volume (TV), indicating an effect on the overall growth of the trabecular bone (FIG. 6B). The cortical bone, however, was unchanged (FIG. 6C). Interestingly, by looking at the biomechanics analysis, the ultimate force and the yield point were prevented from being reduced due to the ovariectomy. This was in line with the protective effect observed on the energy to fracture and the elastic energy, also not decreased by the ovariectomy (FIG. 6D). This suggests that warm microbiota transplantation could partially prevent the ovariectomy-associated bone fragility and protect against the related fracture risk.

EXAMPLE 2

Discussion

Mammals have been co-evolving in symbiosis with their gut microbiota. The external temperature is a major environmental factor to which an individual needs to constantly adapt. It has recently been described that the gut microbiota participates in the adaptation to cold external temperature (Chevalier et al., 2015, Worthmann et al., 2017, and Zietak et al., 2016). Cold exposure induces major changes in the gut microbial population. When transplanted into germ-free animals, this cold-microbiota was able to induce thermogenic activation of beige and brown adipose tissue. The present disclosure shows that warm exposure also induces changes in the bacterial composition measured in the feces, however, to a lesser extent than the one observed after cold. Transplantation of this warm microbiota into germ-free mice was sufficient to blunt the thermogenesis and decrease Ucp1 expression in subcutaneous adipose tissue. This is in line with additional interventions that promote white adipose tissue browning mediated by the gut microbiota composition, such as microbiota depletion (Suarez-Zamorano et al., 2015) or caloric restriction (Fabbiano et al., 2018). Trying to identify common bacteria decreased after cold or caloric restriction and increased after warm may help researchers to understand if a specific bacterial population could be responsible for the adipose tissue whitening. Alteration of these bacterial populations by phage therapy or by transplantation experiments in order to promote adipose tissue browning may be an appealing therapeutic target in the context of obesity.

During warm temperature exposure, mammals dissipate the heat through an increased vasodilatation. This is associated with an elongation of the tail and ear in rodents in order to maximize the surface area for heat dissipation (Alhilli and Wright, 1983 and Ashoub, 1958). Warm exposure during development is also causing elongation of the limbs such as the tibias and the femur (Serrat et al., 2008). The present disclosure illustrates that elevated temperature at a later stage of the development (starting at 8 weeks of age) improves the structural volume of bones of the limbs, especially in the trabecular bone. This phenomenon is already visible after one month of warm exposure in males. After two months of warm exposure in females, the increased trabecular proportion is reflected in the biomechanical resistance of the bone where the yield point and the ultimate stress are improved during a three-point bending test. Sexual dimorphism regarding bone remodeling is well documented (de Bakker et al., 2018). In line with this, the present data show that both sexes display bone remodeling upon warm exposure, but only female mice have improved biomechanical properties.

The effect of the warm temperature was mediated in part by the gut microbiota. Specifically, the "warm" microbiota transplantation displayed increased cortical bone structural volume and tendency towards enhanced trabecular volume. This led to a moderate improvement of the bone mechanical resistance. Interestingly, this phenomenon is relatively rapid since these effects are already observed as early as 20 days after the transplantation. This was associated with an increased glucose uptake in the femur in line with an increased need for fueling the bone remodeling process. Warm microbiota transplantation into germ-free mice leads to increased volume in both trabecular and cortical bone. However, the warm temperature exposure on conventional mice did not show any effect on the cortical bone. Germ-free mice were observed to have an increased trabecular and cortical bone volume compared to conventionally raised animals. When colonized with microbiota, the germ-free mice show a reduction of these parameters (Sjogren et al., 2012). Transplantation of warm microbiota in germ-free mice may prevent the decrease in cortical bone density compared with the conventional, RT-transplanted animals. If warm exposure may thus be used in treating or preventing the bone loss in a pathological condition such as osteoporosis. An ovariectomized mice model was used mimicking the post-menopausal osteoporosis in humans. Warm exposure was indeed able to prevent the bone loss induced by ovariectomy at both trabecular and cortical level. This was also transposed to the mechanical resistance of the bone, where osteoporosis induced fragility was prevented by warm exposure. Interestingly, these effects observed in the tibias were also present in the caudal vertebra where warm exposure prevented the trabecular bone loss in the ovariectomized mice. This indicates a protective effect of the warmth on long bones but also vertebra. Knowing that the associated risk fracture in human affected by osteoporosis is mainly related to the hip (femoral neck) and vertebrae (Bianchi et al., 2005), this supports the idea that warm exposure can be used as a therapeutic intervention to reduce the post-menopausal osteoporosis.

Other approaches may also be used to treat osteoporosis. For example, germ-free mice were protected against osteoporosis induced by GnRH agonist (Li et al., 2016). In the present disclosure, it is shown that recurrent transplantation of warm microbiota into ovariectomized mice was sufficient to prevent bone fragility and improve the trabecular bone structural parameters. The main changes in the bacterial population observed were an increase in the genera *Clostridialeace*-assimilate, *Lactobacillus*, and *Parabacteroides*. The beneficial effect observed with the warm microbiota might be mediated by the increased abundance of the *Lactobacillus* genera. However, the present disclosure shows that the increased *Lactobacillus* genus of the warm microbiota was not efficiently transplanted in the germ-free mice. Still, mice displayed an improvement in bone proportion after structural analysis and moderate improvement in bone mechanical resistance. These results support the idea that other bacterial population changes are responsible for this improvement and identifying them may be included in a probiotic mix for the treatment or prevention of osteoporosis.

The present disclosure illustrates that the gut microbiota is modulated after warm temperature exposure and that it is symbiotically participating in the regulation of the temperature adaptation by decreasing the thermogenic program in the adipose tissue. Additionally, it was uncovered that warm exposure has a positive effect on the bone volume and mechanical resistance in health and in the context of a post-menopausal osteoporosis model. Finally, it was shown that the beneficial effects observed on the bone after warm exposure were at least partially mediated by the gut microbiota changes. Osteoporosis is a highly prevalent bone metabolic disease in the older population and often diagnosed only after the first fracture. Treatments such as warm exposure or probiotic ingestion may be feasible therapeutic approaches in the prevention of this disease.

EXAMPLE 3

Materials and Methods

Animals: All C57BL/6J mice were purchased from Janvier Labs, and kept in a specific pathogen-free (SPF) facility in individually ventilated cages, or in a conventional facility with open cages covered with filter lids. All the mice were in a 12 h day/night cycle and fed a standard chow diet (16.2 MJ/kg Gross Energy; 9 kJ % Fat, 33 kJ % Protein, 58 kJ % Carbohydrates, V1534-727, S sniff, Germany). Germ-free mice of C57BL/6 background were bred and obtained from the germ-free facility of the University of Bern and transplanted with donor microbiota upon arrival in the SFP facility. All the mice were either male and entered the experiment at 8 weeks of age, or female starting at 16 weeks of age (for the ovariectomy experiment). Acclimatized animals were allocated into groups based on their body weight to ensure equal starting points. Warmth exposure was done at 34° C. in a light and humidity-controlled climatic chamber (TSE, Germany) in SPF conditions using individually ventilated cages, or with a temperature-controlled chamber MEDI1300 from Froilabo for the conventional facility. The 34° C. like pair-fed animals were kept at room temperature and fed an equal amount to the warm exposed animals. This is equivalent to ~25% less than RT ad libitum fed, and the food was provided each day at 6 pm. All mice were sacrificed after 5 h fasting. 500 µl of blood was taken from terminally anaesthetized mice in tubes with 10 µl of 0.5 mM EDTA, 4 µl of aprotinin (1.3%), and 4 µl of DPP-IV (10 mM), and plasma stored at −80° C. Samples for RNA isolation were stored in RNA later solution (Invitrogen ref AM7020). Bone samples for CT-scan analysis were stored in a humid package at −20° C., samples for histology in 4% PFA and all other samples snap-frozen in liquid nitrogen. The tail length was measured with a ruler from the tip of the tail to the limit between fur and skin. All animal experiments were approved by the Swiss federal and Geneva cantonal authorities for animal experimentation (Office Vétérinaire Fédéral and Commission Cantonale pour les Expériences sur les animaux de Genève).

Gut microbiota profiling: At the end of the experiment, fecal samples were collected in sterile tubes and immediately frozen and kept at −80° C. Cecal samples were collected after sacrifice of the mice, snap frozen and conserved at −80° C. Fecal and cecal bacterial DNA was then extracted using the PowerFecal DNA Kit (Qiagen, Ref. 12830-50) and the 16SrDNA library was built following the standardized protocol from the earth microbiome project (Caporaso et al., 2012 and Caporaso et al., 2011). Basically, DNA was amplified with QuantaBio 5Prime HotMasterMix using barcoded universal bacterial primers targeting variable region V4 of 16SrRNA gene (515F-806R barcoded primers, Illumina) 806 Reverse Primer GGACTACNVGGGTWTCTAAT (SEQ ID NO: 1)-515 Forward Primer GTGYCAGCMGCCGCGGTAA (SEQ ID NO: 2). 2 ng of template was used and the PCR conditions included an initial denaturation at 94° C. for 3', followed by 35 cycles of denaturation at 94° C. for 45", annealing at 50° C. for 1', and extension at 72° C. for 90", with a final extension at 72° C. for 10'. Each PCR was performed in triplicate later combined and quality checked on an agarose gel. Each PCR amplification was then quantified with Quant-iT PicoGreen dsDNA Assay with SpectraMax Gemini XPS microplate reader and pooled to an equal amount of 200 ng per sample to form the library. The library was purified using QlAquick PCR purification Kit (Qiagen, Ref. 28104), and sequenced from both ends on Illumina MiSeq (kit v2) to generate 2×250 bp paired-end reads (Illumina, San Diego, Calif., USA). Demultiplexed FASTQ files were generated using the MiSeq reporter software. Qiime version 1.9.1 was used for follow-up analysis. Demultiplexed files were paired with a minimum overlap of 200 reads, and barcodes removed from the sequence. Sequences were quality filtered with Phred score of 33 and chimeric sequences removed using Usearch61. OTUs were identified using the pick_open_reference_otus command against the Greengenes 13.8 database clustered at 97%. For the downstream analysis, the number of reads per sample was rarefied to the lowest count in any sample (30000).

Temperature measurement: Body temperature was read with a FLIR E60 (FLIR, UK) infrared camera at 40 cm distance, perpendicular to the region of interest. The body temperature was measured at the eye and the tail temperature was measured as the highest temperature point of the tail. The data were analyzed with the FLIR Tools+software.

Glucose uptake under glucose stimulated condition: Glucose uptake in tissues during GTT was measured after intraperitoneal injection of 2 mg/kg of D-glucose spiked with 2-[14C] deoxyglucose, after a 6 h fast. 45 min later, mice were sacrificed and tissues rapidly harvested for radioactivity measurement.

Glucose uptake measured by positron emission tomography-computed tomography (PET-CT): Mice were anaesthetized with 2% isoflurane and injected in the venous sinus with 4-5 megabecquerel (MBq) [18F]FDG. 10 min prior to PET scan, mice were subjected to CT scans in a Triumph microPET/SPECT/CT system (TriFoil). Images were obtained at 80 peak kilovoltage (kVp) and 160 mA, and 1,024 projections were acquired during the 360° rotation with a field of view of 71.3 mm (1.73 magnification). After 20 min of [18F]FDG uptake, PET scans were performed for a total duration of 10 min (Fabbiano et al., 2016). The software Osirix (Pixmeo) was used to quantitatively analyze the datasets and generate pictures.

Ovariectomy: Mice were anesthetised with Xylazin/Ketamin (injection of 120 µl of a mixture of 120 mg/kg ketamine and 16 mg/kg xylazine) and shaved below the ribs on the back side. Betadine was applied to the area for appropriate disinfection. After a 1-2 cm incision through the skin and the muscle layer just below the ribs, the ovary was localized, the fallopian tube ligated with dissolving suture and the ovary removed. The muscle layer was sutured with dissolving suture, the wound closed with staples and disinfected. The same procedure was performed on the other side. A dose of Tamgesic was administered 4 hours after the surgery, and the staples were removed 7 days after the surgery under isoflurane anaesthesia. The sham-operated animals underwent the same procedure, without ligating the fallopian tube and the ovary excision.

Microbiota transplantation: Upon arrival, germ-free mice were manipulated in aseptic conditions and immediately colonized by gavaging them with cecal content of the appropriate donor. 500 µL, of freshly collected cecal contents from donors (1 month exposed to 34° C. or RT-controls) were pooled and suspended in 5 mL of anaerobic PBS, to make a gavage mixture for each group of colonized mice. Each mouse was orally gavaged with 100 µL of the solution upon arrival and 2 days later. Animals were kept for 7 days in dirty cages from the respective donor groups. For microbiota transplantation of the ovariectomized mice experiment (with a conventional microbiota already present), fecal pellets of the donors were freshly collected every 2 days and immediately homogenized in 1 mL of anaerobic PBS. After a short centrifugation (300 g, 30 sec), the supernatant was then immediately gavaged to the respective recipient. In this condition, one cage of donors (1 pellet per mouse from both mice) was used to repopulate 1 cage of recipients. Each recipient was receiving 200 µL of the donor mixture every 2 days.

Micro-CT analysis: For the better sensitivity of the scan, mice were also scanned with a micro-CT (VivaCT40/Scanco system; Zurich, Switzerland). The limbs were scanned in vivo before the ovariectomy to determine the basal state.

After xylazine/ketamine anaesthesia, mice limbs were scanned for 18 min. Final scans were performed post-mortem on isolated bones. Subsequent analysis was performed using micro-CT software. For the femoral and tibial trabecular region, one hundred slices were analyzed starting from 50 slices below the distal growth plate. Femoral and tibial cortical structure was assessed through 60 continuous CT slides (600 µm) from the bone midshaft. Images were segmented using an adaptative-iterative threshold approach, rather than a fixed threshold. Morphometric variables were computed from binarized images using direct, 3D techniques that do not rely on prior assumptions about the underlying structure. For trabecular bone regions, the bone volume/total volume (BV/TV) was assessed. For cortical bone at the femoral and tibial midshaft, the cortical bone volume ($mm^3$) was measured and the average cortical thickness named cortical width (µm).

Biomechanical analysis of the bones: A 3-points bending test was used to measure biomechanical parameters of the bone. Tibias were placed on two supports separated by a distance of 9.9 mm and the load was applied to the midpoint of the shaft (creating a 3-points bending). Mechanical resistance to failure (displacement and load applied) was measured using a servo-controlled electromechanical system (Instron 1114, Instron corp., High Wycombe, UK) with actuator displaced at 2 mm/minute. Ultimate force (maximal load, measured in Newtons, N), Yield point (N), stiffness (elastic energy, N/mm), and energy to fracture (surface under the curve of the plastic region, N*mm) were calculated. Young's modulus (MPa) was determined by the equation previously described (McMillan et al., 1989).

Histological analyses: Tissues were excised, fixed in 4% paraformaldehyde (Sigma-Aldrich), paraffin embedded, cut in 5 µm-thick sections and stained with H&E using standard techniques.

RNA extraction, reverse transcription and real-time PCR: Upon collection, tissues were stored in 1 mL RNAlater and immediately processed for RNA extraction for the bone tissues or stored at −80° C. For RNA extraction, tissues were placed in 2 mL Eppendorf tubes containing 1 mL Trizol (Thermo Fisher Scientific) and mechanically disaggregated using the bead-based TissueLyser equipment (Qiagen) by shaking for 40 seconds at 30 Hz in presence of a silicate bead for the bone and a metal bead for the other tissues. After brief centrifugation to remove tissue debris (3 minutes, 12000 g, 4° C.), 200 µL, chloroform was added, samples were shaken and centrifuged for 15 minutes at 12000 g at 4° C. The chloroform phase was collected, mixed with 500 µL isopropanol and centrifuged again as before. The pellet obtained was washed twice with 70% ethanol and ultimately resuspended in 50 µL PCR-grade water. For retro-transcription, 1 µg RNA was used per sample using the High-Capacity cDNA Reverse Transcription Kit (Applied Biosystems). qPCR were performed on a LightCycler 480 machine (Roche) with SYBR Green-based detection (Thermo fisher scientific). The primer sequences are the following.

| Gene | Forward primer | Reverse primer |
| --- | --- | --- |
| Uncoupling protein 1 (Ucp1) | GCATTCAGAGGCAAATCAGC (SEQ ID NO: 3) | GCCACACCTCCAGTCATTAAG (SEQ ID NO: 4) |
| Cell Death-Inducing DFFA-Like Effector A (CIDEA) | TGCTCTTCTGTATCGCCCAGT (SEQ ID NO: 5) | GCCGTGTTAAGGAATCTGCTG (SEQ ID NO: 6) |
| Peroxisome proliferator-activated receptor gamma coactivator 1-alpha (PGC1a) | CCCTGCCATTGTTAAGACC (SEQ ID NO: 7) | TGCTGCTGTTCCTGTTTTC (SEQ ID NO: 8) |
| Iodothyronine Deiodinase 2 (Dio2) | CAGTGTGGTGCACGTCTCCAATC (SEQ ID NO: 9) | TGAACCAAAGTTGACCACCAG (SEQ ID NO: 10) |
| TATA Box binding Protein (TBP) | GAAGCTGCGGTACAATTCCAG (SEQ ID NO: 11) | CCCCTTGTACCCTTCACCAAT (SEQ ID NO: 12) |
| Beta-2-Microglobulin (B2m) | TTGTCTCACTGACCGGCCT (SEQ ID NO: 13) | TATGTTCGGCTTCCCATTCTCC (SEQ ID NO: 14) |
| glycéraldéhyde-3-phosphate déshydrogénase (Gapdh) | GGGTTCCTATAAATACGGACTGC (SEQ ID NO: 15) | CCATTTTGTCTACGGGACGA (SEQ ID NO: 16) |
| Peroxisome Proliferator Activated Receptor Alpha (PPARa) | AGAGCCCCATCTGTCCTCTC (SEQ ID NO: 17) | ACTGGTAGTCTGCAAAACCAAA (SEQ ID NO: 18) |
| PR domain containing 16 (Prdm16) | CAGCACGGTGAAGCCATT (SEQ ID NO: 19) | GCGTGCATCCGCTTGTG (SEQ ID NO: 20) |
| G-protein-coupled bile acid receptor (TGR5) | CCTGTCAGTCTTGGCCTATGAG3 (SEQ ID NO: 21) | GCCCAATGAGATGAGCGATA3 (SEQ ID NO: 22) |

Echo-MRI: Body weight composition was determined using an EchoMRI-700 equipment.

EXAMPLE 4

Transplantation of Specific Warm-Adapted Microbiota Exerts a Protective Role Against Osteoporosis In Vivo In the above examples, data is provided showing that that warm exposure improves bone strength and protects against ovariectomy-induced osteoporosis in a post-menopausal mouse model. This data also shows that warm exposure changes the microbiota composition, and that transplantation of this warm-adapted microbiota in ovariectomized mice exerts protective role against osteoporosis.

This work was extended by analyzing the microbiota composition associated with improved osteoporosis using a bioinformatics analysis, and several bacteria we selected for further in vivo analysis. Using recurrent transplantation of these single microbes (as specified in the Methods section below) into post-menopausal, ovariectomy-induced osteoporosis mice model, 3 bacteria were identified that can be used as probiotic treatment to prevent osteoporosis. Specifically, *Lactobacillus gasseri, Lactobacillus reuteri* (used as positive control) and heat-inactivated (HI) *Parabacteroides goldsteinii* were observed to strengthen bones in an in vivo mouse model, that is they were observed to reduce or prevent the reduction in ultimate force and increased displacement when biomechanical tests were performed on femurs (FIGS. 7A-B). These data indicate that transplantation of these single bacteria can lead to overall improvement in the bone strength associated with reduced ductility, thus preventing the ovariectomy-induced increase in displacement and bone fragility. In addition, data were obtained showing that these bacteria may help reduce or prevent trabecular bone BV/TV loss (FIG. 7C). It is anticipated that mixtures of these bacteria may similarly or further improve strengthening of bones and/or may further be used to treat osteoporosis.

Methods

Animals: All C57BL/6J mice were purchased from Janvier Labs, and kept in a specific pathogen-free (SPF) facility in individually ventilated cages. All the mice were in a 12 h day/night cycle and fed a standard chow diet (16.2 MJ/kg Gross Energy; 9 kJ % Fat, 33 kJ % Protein, 58 kJ % Carbohydrates, V1534-727, Ssniff, Germany). All the mice were either male and entered the experiment at 8 weeks of age, or female starting at 16 weeks of age (for the ovariectomy experiment). Acclimatized animals were allocated into groups based on their body weight to ensure equal starting points. Warmth exposure was done at 34° C. in a light and humidity-controlled climatic chamber (TSE, Germany) in SPF conditions using individually ventilated cages All mice were sacrificed after 5 h fasting. Bone samples for CT-scan and biomecanics analysis were stored in a humid package at −20° C. All animal experiments were approved by the Swiss federal and Geneva cantonal authorities for animal experimentation (Office Vétérinaire Fédéral and Commission Cantonale pour les Expériences sur les animaux de Genève).

Ovariectomy: Mice were anesthetised with Xylazin/Ketamin (injection of 120 µl of a mixture of 120 mg/kg ketamine and 16 mg/kg xylazine) and shaved below the ribs on the back side. Betadine was applied to the area for appropriate disinfection. After a 1-2 cm incision through the skin and the muscle layer just below the ribs, the ovary was localized, the fallopian tube ligated with dissolving suture and the ovary removed. The muscle layer was sutured with dissolving suture, the wound closed with staples and disinfected. The same procedure was performed on the other side. A dose of Tamgesic was administered 4 hours after the surgery, and the staples were removed 7 days after the surgery under isoflurane anaesthesia. The sham-operated animals underwent the same procedure, without ligating the fallopian tube and the ovary excision.

Microbiota transplantation: For microbiota transplantation of the ovariectomized mice experiment (with a conventional microbiota already present), fecal pellets of the donors were freshly collected every 2 days and immediately homogenized in 1 ml of anaerobic PBS. After a short centrifugation (300 g, 30 sec), the supernatant was then immediately gavaged to the respective recipient. In this condition, one cage of donors (1 pellet per mouse from both mice) was used to repopulate 1 cage of recipients. Each recipient was receiving 200 µl of the donor mixture every 2 days.

Single microbe transplantation: *Lactobacillus gasseri* (DSM 20604) and *Parabacteroides goldsteinii* (DSM 19948) were pushased from DSMZ. *Lactobacillus reuteri* (PTA-6475) and *Akkermansia muciniphila* (BAA835) was purchased from ATCC. *Lactobacillus gasseri* and *reuteri* were grown in MRS (deMan, Rogosa and Sharpe, USbiological Life Sciences, L1021-01) medium, *P. goldsteinii* in anaerobe basal broth (Thermo Scientific Oxoid Microbiology Products, CM0957), and *A. muciniphila* in SCHAEDLER Broth+Vitamin K3, (Biomerieux ref 42106) in an anaerobic incubator (Coy vinyl anaerobic chamber type C) set at 37° C. with a gas mix of 5% CO2, 5% H and 90% N. Freshly prepared bacteria were diluted in anaerobic PBS to a final concentration equivalent to 10D at 600 nm. 300 ul of this suspension was gavaged every second day to the ovariectomized mice, starting 3 days post-surgery for 2 month until the sacrifice. *P. goldsteinii* preparation was heat inactivated with 100° C. for 15 min before the gavage, and the inactivation was confirmed.

Micro-CT analysis: Mice were scanned with a micro-CT (VivaCT40/Scanco system; Zurich, Switzerland). The limbs were scanned in vivo before the ovariectomy to determine the basal state. After Xylazine/Ketamine anaesthesia, mice limbs were scanned for 18 min. Final scans were performed post-mortem on isolated bones. Subsequent analysis was done using micro-CT software. For the femoral and tibial trabecular region, one hundred scans (i.e., scan "slices") were analyzed, starting from 50 slices below the distal growth plate. Femoral and tibial cortical structure was assessed through 60 continuous CT slides (600 µm) from the bone midshaft. Images were segmented using an adaptive-iterative threshold approach, rather than a fixed threshold. Morphometric variables were computed from binarized images using direct, 3D techniques that do not rely on prior assumptions about the underlying structure. For trabecular bone regions, we assessed the bone volume/total volume (BV/TV). For cortical bone at the femoral and tibial midshaft, we measured the cortical bone volume ($mm^3$) and the average cortical thickness named cortical width (µm).

Biomechanical analysis of the bones: We used a 3-points bending test to measure biomechanical parameters of the bone. Femurs were placed on two supports separated by a distance of 9.9 mm and the load was applied to the midpoint of the shaft (creating a 3-points bending). Mechanical resistance to failure (displacement and load applied) was measured using a servo-controlled electromechanical system (Instron 1114, Instron corp., High Wycombe, UK) with actuator displaced at 2 mm/minute. Ultimate force (maximal load, measured in Newtons [N]), Yield point (N), stiffness (elastic energy, N/mm), and energy to fracture (surface under the curve of the plastic region, N*mm) were calculated. Young's modulus (MPa) was determined.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abreu-Vieira et al., *Molecular Metabolism*, 4(6): p. 461-470, 2015.
Alhilli and Wright, *British Journal of Experimental Pathology*, 64(1): p. 34-42, 1983.
Ashoub, M. A., *Nature*, 181(4604): p. 284, 1958.
Bianchi et al., *Health Qual Life Outcomes*, 3: p. 78, 2005.
Britton et al., *Journal of Cellular Physiology*, 2014. 229(11): p. 1822-1830, 2014.
Calinescu et al., *Eur J Pharm Biopharm.*, 60(1):53-60, 2005.
Caporaso et al., *Proceedings of the National Academy of Sciences of the United States of America*, 108: p. 4516-4522, 2011.
Caporaso et al., *Isme Journal*, 6(8): p. 1621-1624, 2012.
Chelakkot et al., *Experimental & Molecular Medicine* volume 50, page e450, 2018.
Chevalier et al., *Cold. Cell*, 163(6): p. 1360-74, 2015.
Choi et al., *Sci Rep*, 5: 15878, 2015.
Cui et al., *Physiol Rep*, 4(10), 2016.
Dar et al., *Bone Rep*, 8: p. 46-56, 2018.
de Bakker et al., *J Biomech*, 2018.
Derrien et al., *Int J Syst Evol Microbiol*, 54: 1469-1476, 2004.
Devlin et al., *Journal of Bone and Mineral Research*, 2010. 25(9): p. 2078-2088, 2010.
Ellis and Kuehn, *Microbiol Mol Biol Rev.*, 74: 81-94, 2010.
Fabbiano et al., *Cell metabolism*, In press, 2018.
Fabbiano et al., *Cell Metab*, 24(3): p. 434-46, 2016.
Govander et al., *AAPS PharmSciTech*, 15(1):29-43, 2014.
Harland, S. C., *Nature*, 186(4723): p. 446-446, 1960.
Hong et al., *Allergy*, 66: 351-359, 2011.
Horstman and Kuehn, *J Biol Chem.*, 277: 32538-32545, 2002.
Hussan et al., *Journal of Pharmacy* 2(6):5-11, 2012.
Iwaniec and Turner, *J Endocrinol*, 2016. 230(3): p. R115-30.
Iwasa et al., *Horm Behav*, 97: p. 25-30, 2018.
Kaiyala et al., *Plos One*, 7(8), 2012.
Kang et al., *PLoS ONE*, 8: e76520, 2013.
Kim et al., *Clin Exp Allergy*, 43: 443-454, 2013.
Kuehn and Kesty, *Genes Dev.*, 19: 2645-2655, 2005.
Lee et al. *Proteomics*, 7: 3143-3153, 2007.
Lee et al., *Proteomic*, 9: 5425-5436, 2009.
Legroux-Gerot et al., *Calcified Tissue International*, 81(3): p. 174-182, 2007.
Li, et al., *Journal of Clinical Investigation*, 126(6): p. 2049-2063, 2016.
Mcmillan et al., *Calcified Tissue International*, 44(6): p. 399-405, 1989.
Meyer et al., *Frontiers in Physiology*, 8, 2017.
Nilsson et al., *J Intern Med*, 2018.
Ohlsson and Sjogren, *Trends Endocrinol Metab*, 2015. 26(2): p. 69-74.
Reginster and Burlet, *Bone*, 38(2): p. 4-9, 2006.
Romsos, et al., *Metabolism-Clinical and Experimental*, 34(10): p. 931-937, 1985.
Sanderson et al., *Journals of Gerontology Series a-Biological Sciences and Medical Sciences*, 52(1): p. B20-B25, 1997.
Serrat, et al., *Proceedings of the National Academy of Sciences of the United States of America*, 105(49): p. 19348-19353. 2008.
Serrat, et al., *Journal of Orthopaedic Research*, 33(5): p. 692-698, 2015.
Sjogren et al., *J Bone Miner Res*, 27(6): p. 1357-67, 2012.
Sozen et al., *European Journal of Rheumatology*, 4(1): p. 46-56, 2017.
Suarez-Zamorano et al., Nat Med, 2015. 21(12): p. 1497-1501, 2015.
Villareal *Arch Intern Med*, 166(22): p. 2502-10, 2006.
Wilson et al. *Front Cell Infect Microbiol*. 9: 2, 2019.
Worthmann *Nat Med*, 23(7): p. 839-849, 2017.
Wu et al., *Hirsutella sinensis, Gut.* 68(2):248-262, 2019.
Wright, 1983.
Yang et al., 235(1-2):1-15, 2002.
Zietak *Cell Metabolism*, 23(6): p. 1216-1223, 2016.

What is claimed is:

1. A method of treating a bone disease in a mammalian subject, comprising administering a pharmaceutical or probiotic composition to the gastrointestinal system of the subject;
wherein the composition comprises an effective amount of an inactivated *Parabacteroides goldsteinii*; and
wherein the bone disease is osteoporosis.

2. The method of claim 1, wherein the composition further comprises *Lactobacillus gasseri* or *Lactobacillus reuteri*.

3. The method of claim 1, wherein the *Parabacteroides goldsteinii* is heat-inactivated.

4. The method of claim 1, wherein the composition further comprises extracellular vesicles from *Lactobacillus gasseri*, extracellular vesicles from *Lactobacillus reuteri*, or extracellular vesicles from *Parabacteroides goldsteinii*.

5. The method of claim 4, wherein the *Parabacteroides goldsteinii* is heat-inactivated.

6. The method of claim 1, wherein the composition comprises from about $1 \times 10^8$ to about $1 \times 10^{13}$ cfu of the inactivated *Parabacteroides goldsteinii*.

7. The method of claim 1, wherein the pharmaceutical or probiotic composition further comprises *Clostridialeace*-assimilate spp., *Lactobacillus* spp., *Bifidobacteriaceae* spp., and/or *Parabacteroides* spp.

8. The method of claim 1, wherein the pharmaceutical or probiotic composition further comprises 1. *Lactobacillus* spp. and *Parabacteroides* spp., or 2. *Lactobacillus* spp. and *Bifidobacteriaceae* spp.

9. The method of claim 1, wherein the pharmaceutical or probiotic composition further comprises *Clostridialeace*-assimilate spp., *Lactobacillus* spp., and *Parabacteroides* spp.

10. The method of claim 9, wherein ratios of bacteria in the *Clostridialeace*-assimilate spp., *Lactobacillus* spp., and *Parabacteroides* spp. are: about 10-40% *Clostridialeace*-assimilate spp., about 40-60% *Lactobacillus* spp., and about 10-40% *Parabacteroides* spp.

11. The method of claim 10, wherein ratios of bacteria in the *Clostridialeace*-assimilate spp., *Lactobacillus* spp., and *Parabacteroides* spp. are: about 10-35% *Clostridialeace*-assimilate spp., about 40-60% *Lactobacillus* spp., and about 20-30% *Parabacteroides* spp.

12. The method of claim 1, wherein the pharmaceutical or probiotic composition further comprises *Bifidobacteriaceae* or *Akkermansia muciniphila*.

13. The method of claim 12, wherein the *Bifidobacteriaceae* is *Bifidobacterium longum*.

14. The method of claim 1, wherein the pharmaceutical or probiotic composition comprises a live bacteria.

15. The method of claim 1, wherein the inactivated *Parabacteroides goldsteinii* comprises heat-inactivated bacteria.

16. The method of claim 1, wherein the inactivated *Parabacteroides goldsteinii* comprises frozen or dried bacteria.

17. The method of claim 1, wherein the composition further comprises extracellular vesicles from *Clostridialeace*-assimilate spp., extracellular vescicles from *Lactobacillus* spp., extracellular vescicles from *Bifidobacteriaceae* spp., or extracellular vesicles from *Parabacteroides* spp.

18. The method of claim 1, wherein the pharmaceutical or probiotic composition is administered orally, colonically, via enema, via an orogastric tube, or via a nasogastric tube.

19. The method of claim 1, wherein the pharmaceutical or probiotic composition is resistant to degradation in the stomach but releases bacteria in the small intestine and/or large intestine of the subject.

20. The method of claim 1, wherein the pharmaceutical or probiotic composition comprises an enteric coating, chitosan-alginate beads, or a hydrogel.

21. The method of claim 20, wherein the enteric coating is a fatty acid, a wax, a shellac, a plastic such as a phthalate, CAP, CAT, PVAP, HPMCP, or a plant fiber.

22. The method of claim 1, wherein the pharmaceutical or probiotic composition does not comprise an enteric coating.

23. The method of claim 1, wherein the pharmaceutical or probiotic composition is a tablet or capsule.

24. The method of claim 1, wherein the subject is a human.

25. The method of claim 1, wherein the method comprises obtaining warm microbiota from a super donor or a separate healthy subject, wherein the warm microbiota comprises a bacteria from the group consisting of *Clostridialeace*-assimilate spp., *Lactobacillus* spp. *Bifidobacteriaceae* spp., and *Parabacteroides* spp.

26. The method of claim 25, wherein the warm microbiota is frozen after the obtaining and prior to administering to the subject.

27. The method of claim 1, wherein the method comprises obtaining warm microbiota from the subject during the spring or summer and administering the warm microbiota to the subject during the winter.

28. The method of claim 27, wherein the warm microbiota is frozen after the obtaining and prior to administering to the subject.

29. The method of claim 1, wherein the inactivated *Parabacteroides goldsteinii* in the composition has been purified or cultured.

30. the method of claim 1, wherein the osteoporosis results from post-menopausal estrogen deficiency.

\* \* \* \* \*

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial sequence
<220> FEATURE:
<223> OTHER INFORMATION: Synthetic primer
<220> FEATURE:
<221> NAME/KEY: misc_feature
<222> LOCATION: (8)..(8)
<223> OTHER INFORMATION: n is a, c, g, or t
```

<400> SEQUENCE: 1
ggactacnvg ggtwtctaat                                            20

<210> SEQ ID NO 2
<211> LENGTH: 19
<212> TYPE: DNA
<213> ORGANISM: Artificial sequence
<220> FEATURE:
<223> OTHER INFORMATION: Synthetic primer

<400> SEQUENCE: 2
gtgycagcmg ccgcggtaa                                             19

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
gcattcagag gcaaatcagc                                            20

<210> SEQ ID NO 4
<211> LENGTH: 21
<212> TYPE: DNA
<213> ORGANISM: Artificial sequence
<220> FEATURE:
<223> OTHER INFORMATION: Synthetic primer

<400> SEQUENCE: 4
gccacacctc cagtcattaa g                                          21

<210> SEQ ID NO 5
<211> LENGTH: 21
<212> TYPE: DNA
<213> ORGANISM: Artificial sequence
<220> FEATURE:
<223> OTHER INFORMATION: Synthetic primer

<400> SEQUENCE: 5
tgctcttctg tatcgcccag t                                          21

<210> SEQ ID NO 6
<211> LENGTH: 21
<212> TYPE: DNA
<213> ORGANISM: Artificial sequence
<220> FEATURE:
<223> OTHER INFORMATION: Synthetic primer

<400> SEQUENCE: 6
gccgtgttaa ggaatctgct g                                          21

<210> SEQ ID NO 7
<211> LENGTH: 19
<212> TYPE: DNA
<213> ORGANISM: Artificial sequence
<220> FEATURE:
<223> OTHER INFORMATION: Synthetic primer

<400> SEQUENCE: 7
ccctgccatt gttaagacc                                             19

<210> SEQ ID NO 8
<211> LENGTH: 19
<212> TYPE: DNA
<213> ORGANISM: Artificial sequence
<220> FEATURE:
<223> OTHER INFORMATION: Synthetic primer

<400> SEQUENCE: 8
tgctgctgtt cctgttttc                                          19

<210> SEQ ID NO 9
<211> LENGTH: 23
<212> TYPE: DNA
<213> ORGANISM: Artificial sequence
<220> FEATURE:
<223> OTHER INFORMATION: Synthetic primer

<400> SEQUENCE: 9
cagtgtggtg cacgtctcca atc                                     23

<210> SEQ ID NO 10
<211> LENGTH: 21
<212> TYPE: DNA
<213> ORGANISM: Artificial sequence
<220> FEATURE:
<223> OTHER INFORMATION: Synthetic primer

<400> SEQUENCE: 10
tgaaccaaag ttgaccacca g                                       21

<210> SEQ ID NO 11
<211> LENGTH: 21
<212> TYPE: DNA
<213> ORGANISM: Artificial sequence
<220> FEATURE:
<223> OTHER INFORMATION: Synthetic primer

<400> SEQUENCE: 11
gaagctgcgg tacaattcca g                                       21

<210> SEQ ID NO 12
<211> LENGTH: 21
<212> TYPE: DNA
<213> ORGANISM: Artificial sequence
<220> FEATURE:
<223> OTHER INFORMATION: Synthetic primer

<400> SEQUENCE: 12
ccccttgtac ccttcaccaa t                                       21

<210> SEQ ID NO 13
<211> LENGTH: 19
<212> TYPE: DNA
<213> ORGANISM: Artificial sequence
<220> FEATURE:
<223> OTHER INFORMATION: Synthetic primer

<400> SEQUENCE: 13
ttgtctcact gaccggcct                                          19

<210> SEQ ID NO 14
<211> LENGTH: 22
<212> TYPE: DNA
<213> ORGANISM: Artificial sequence
<220> FEATURE:
<223> OTHER INFORMATION: Synthetic primer

```
<400> SEQUENCE: 14
tatgttcggc ttcccattct cc                                          22

<210> SEQ ID NO 15
<211> LENGTH: 23
<212> TYPE: DNA
<213> ORGANISM: Artificial sequence
<220> FEATURE:
<223> OTHER INFORMATION: Synthetic primer

<400> SEQUENCE: 15
gggttcctat aaatacggac tgc                                         23

<210> SEQ ID NO 16
<211> LENGTH: 20
<212> TYPE: DNA
<213> ORGANISM: Artificial sequence
<220> FEATURE:
<223> OTHER INFORMATION: Synthetic primer

<400> SEQUENCE: 16
ccattttgtc tacgggacga                                             20

<210> SEQ ID NO 17
<211> LENGTH: 20
<212> TYPE: DNA
<213> ORGANISM: Artificial sequence
<220> FEATURE:
<223> OTHER INFORMATION: Synthetic primer

<400> SEQUENCE: 17
agagccccat ctgtcctctc                                             20

<210> SEQ ID NO 18
<211> LENGTH: 22
<212> TYPE: DNA
<213> ORGANISM: Artificial sequence
<220> FEATURE:
<223> OTHER INFORMATION: Synthetic primer

<400> SEQUENCE: 18
actggtagtc tgcaaaacca aa                                          22

<210> SEQ ID NO 19
<211> LENGTH: 18
<212> TYPE: DNA
<213> ORGANISM: Artificial sequence
<220> FEATURE:
<223> OTHER INFORMATION: Synthetic primer

<400> SEQUENCE: 19
cagcacggtg aagccatt                                               18

<210> SEQ ID NO 20
<211> LENGTH: 17
<212> TYPE: DNA
<213> ORGANISM: Artificial sequence
<220> FEATURE:
<223> OTHER INFORMATION: Synthetic primer

<400> SEQUENCE: 20
gcgtgcatcc gcttgtg                                                17
```

```
<210> SEQ ID NO 21
<211> LENGTH: 22
<212> TYPE: DNA
<213> ORGANISM: Artificial sequence
<220> FEATURE:
<223> OTHER INFORMATION: Synthetic primer

<400> SEQUENCE: 21
cctgtcagtc ttggcctatg ag                                              22

<210> SEQ ID NO 22
<211> LENGTH: 20
<212> TYPE: DNA
<213> ORGANISM: Artificial sequence
<220> FEATURE:
<223> OTHER INFORMATION: Synthetic primer

<400> SEQUENCE: 22
gcccaatgag atgagcgata                                                 20
```